(12) United States Patent
Janssen-Heininger et al.

(10) Patent No.: US 8,679,811 B2
(45) Date of Patent: Mar. 25, 2014

(54) TREATMENTS INVOLVING GLUTAREDOXINS AND SIMILAR AGENTS

(75) Inventors: Yvonne M. Janssen-Heininger, Charlotte, VT (US); Niki Lea Reynaert, Maasmechelen (BE); Vikas Anathy, Burlington, VT (US); Scott Aesif, Burlington, VT (US)

(73) Assignees: The University of Vermont and State Agricultural College, Burlington, VT (US); Universiteit Maastricht, Maastricht (NE)

( * ) Notice: Subject to any disclaimer, the term of this patent is extended or adjusted under 35 U.S.C. 154(b) by 635 days.

(21) Appl. No.: 12/664,108

(22) PCT Filed: Jun. 10, 2008

(86) PCT No.: PCT/US2008/007246
§ 371 (c)(1),
(2), (4) Date: Jun. 21, 2010

(87) PCT Pub. No.: WO2008/154012
PCT Pub. Date: Dec. 18, 2008

(65) Prior Publication Data
US 2010/0266566 A1    Oct. 21, 2010

Related U.S. Application Data

(60) Provisional application No. 60/934,129, filed on Jun. 11, 2007.

(51) Int. Cl.
*C12N 9/02* (2006.01)
(52) U.S. Cl.
USPC ........................................ 435/189; 424/94.4
(58) Field of Classification Search
USPC .......................................................... 435/77
See application file for complete search history.

(56) References Cited

U.S. PATENT DOCUMENTS

| | | | |
|---|---|---|---|
| 6,379,664 B1 | 4/2002 | Lou et al. | |
| 6,806,057 B2 | 10/2004 | Snyder et al. | |
| 7,001,738 B2 | 2/2006 | Snyder et al. | |
| 2005/0026227 A1 | 2/2005 | Snyder et al. | |
| 2005/0238734 A1 | 10/2005 | Janssen et al. | |
| 2006/0205771 A1* | 9/2006 | Noble et al. | 514/310 |
| 2008/0014595 A1 | 1/2008 | Janssen-Heininger et al. | |

FOREIGN PATENT DOCUMENTS

| WO | WO 2005/101019 | 10/2005 |
|---|---|---|
| WO | WO 2008/154012 | 12/2008 |

OTHER PUBLICATIONS

Anathy Vikas et al., "Redox amplification of apoptosis by caspase-dependent cleavage of glutaredoxin 1 and S-glutathionylation of Fas" The Journal of Cell Biology, vol. 184(2), 241-252, 2009.
Argyrou et al. 2004, Prog Nucleic Acid Res Mol Biol 78:89-142.
Bertlett et al., "Protein Oxidation in Aging, Disease, and Oxidative Stress," Journal of Biological Chemistry, 1997 272 33(20313-20316).
Bishop C. et al., "A Pilot Study of the Effect of Inhaled Buffered Reduced Glutathione on the Clinical Status of Patieents with Cystic Fibrosis," www.chestjournal.org, 127 1 (308-317), 2005.
Cheng et al., "Detection of S-glutathionylated proteins by glutathione S-transferase overlay," *Archives of Biochemistry and Biophysics*, 2005 435(42-49).
Chivers et al., "The CXXC Motif: A Rheostat in the Active Site," 1997, Biochemistry 36: 4061-4060.
Erlendsson et al., "*Bacillus subtilis* ResA is a Thiol-Disulfide Oxidoreductase involved in Cytochrome c Synthesis,"JBC 278: 17852-17858.
Fernando M. Rohan et al., "Mitochondrial thioltransferase (glutaredoxin 2) has GSH-dependent and thioredoxin reductase-dependent peroxidase activities in vitro and in lens epithelial cells," The FASEB Journal: Official Publication of the Federation of American Societies for Experimental Biology, vol. 20(4), Dec. 2006, 2645-2647.
Finkel T., "Oxidant signals and oxidative stress," *Current Opinion in Cell Biology*, 2003 15 (247-254).
Giustarini et al., "S-glutathionylation: from redox regulation of protein functions to human diseases," *J. of Cellular and Molecular Medicine*, vol. 8(2), (Apr. 2004) 201-212.
Johansson et al., "Human Mitochondrial Glutaredoxin Reduces S-Glutathionylated Proteins with High Affinity Accepting Electrons from Either Glutathione or Thioredoxin Reductase," 2004, JBC 279: 7537-7543.
Pan Shi et al., "Glutathiolatin regulates tumor necrosis factor-alpha-induced caspase-3 cleavage and apoptosis—Key role for gluaredoxin in the death pathway," Circulation Research, vol. 100(2), Feb. 2007, 213-219.
Reynaert et al., "Dynamic Redox Control of NF" Proceedings of the National Academy of Sciences of the United States of America (2006), vol. 103, 13086-13091.
Reynaert et al., "Modulation of Glutaredoxin-1 Expression in a Mouse Model of Allergic Airway Disease" Am. J. Respir. Cell Mol. Biol., vol. 36, pub. Feb. 2007, 148-151.
Reynaert N. et al., "In situ detection of S-glutathionylated proteins following glutaredoxin-1 catalyzed cysteine derivatization," *Biochimica et Biophyscia Acta* 2006 1760(380-387).

(Continued)

*Primary Examiner* — Anand Desai
*Assistant Examiner* — Rama P Ramanujam
(74) *Attorney, Agent, or Firm* — Wolf, Greenfield & Sacks, P.C.

(57) ABSTRACT

The present invention generally relates to treatments involving glutaredoxins. In one aspect, systems and methods of the invention can be used to treat a subject having an oxidative stress condition, for example, airway inflammation or asthma. In some embodiments, a glutaredoxin may be used to treat a subject. Also provided in certain aspects of the present invention are kits for therapies involving glutaredoxins, methods for promoting such therapies, and the like.

16 Claims, 14 Drawing Sheets

(56) References Cited

OTHER PUBLICATIONS

Sagemark Johan et al., "Redox properties and evolution of human glutaredoxins," Proteins Structure Function and Bioinformatics, vol. 68(4), Jun. 2007, 879-892.

Schulz J. et al., "Glutathione, oxidative stress and neurodegeneration," *Eur. J. Biochem.* 2000 267(4904-4911).

Timmer J C et al., "Caspase substrates" Cell Death and Differentiation, vol. 14(1), Jan. 2007, 66-72.

Watson et al., "Thioredoxin and Its Role in Toxicology" 2004, Toxicological Sci. 78: 3-14.

* cited by examiner

Fig. 2A        Fig. 2B   sham
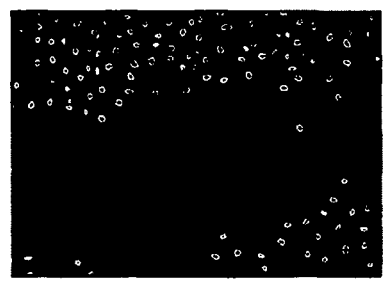
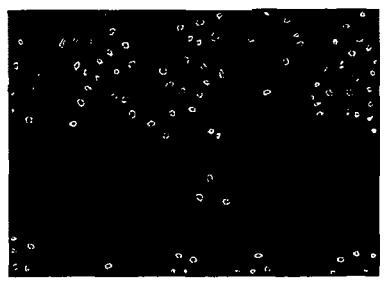
Fig. 2C        Fig. 2D   GRX 500 ng/ml

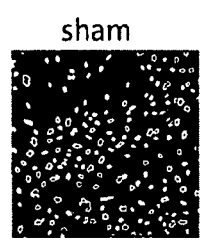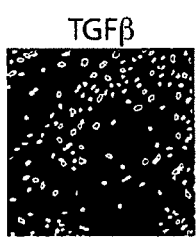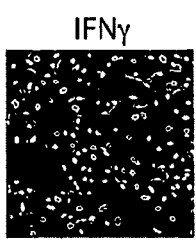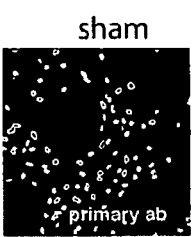
Fig. 5C  Fig. 5D  Fig. 5E  Fig. 5F
GRX1
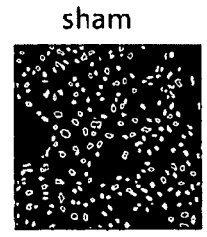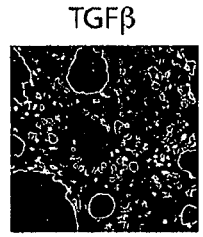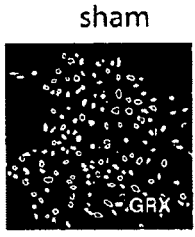
Fig. 5G  Fig. 5H  Fig. 5I  Fig. 5J
P-SSG

Glrx 1

```
                                               *
MAQEFVNCKI QSGKVVVFIK PTCPYCRKTQ EILSQLPFKQ GLLEFVDITA   50
TNNTSAIQDY LQQLTGARTV PRVFIGKDCI GGCSDLISMQ QTGELMTRLK  100
QIGALQL  (SEQ ID NO: 6)                                 107
```

NNTS – ASN (N) glycosylation site - by predict protein (SEQ ID NO: 7)

VFIK PTCPYCRKTQEIL - Glutaredoxin active site - by predict protein (SEQ ID NO: 8)

SGK- PKC Phospho site - by predict protein www.predictprotein.org

*EFVD- Putative caspase cleavage site - prediction not confirmed (SEQ ID NO: 9)

SEQUENCE LISTING

```
<160> NUMBER OF SEQ ID NOS: 9

<210> SEQ ID NO 1
<211> LENGTH: 4
<212> TYPE: PRT
<213> ORGANISM: mus musculus

<400> SEQUENCE: 1

Cys Pro Tyr Cys
1

<210> SEQ ID NO 2
<211> LENGTH: 4
<212> TYPE: PRT
<213> ORGANISM: mus musculus

<400> SEQUENCE: 2

Cys Ser Tyr Cys
1

<210> SEQ ID NO 3
<211> LENGTH: 4
<212> TYPE: PRT
<213> ORGANISM: mus musculus

<400> SEQUENCE: 3

Cys Gly Phe Ser
1

<210> SEQ ID NO 4
<211> LENGTH: 4
<212> TYPE: PRT
<213> ORGANISM: homo sapiens

<400> SEQUENCE: 4

Cys Pro Phe Cys
1

<210> SEQ ID NO 5
<211> LENGTH: 4
<212> TYPE: PRT
```

```
<213> ORGANISM: mus musculus
<220> FEATURE:
<221> NAME/KEY: VARIANT
<222> LOCATION: (3)..(3)
<223> OTHER INFORMATION: Xaa is Selenocysteine

<400> SEQUENCE: 5

Gly Cys Xaa Gly
1                4

<210> SEQ ID NO 6
<211> LENGTH: 107
<212> TYPE: PRT
<213> ORGANISM: mus musculus

<400> SEQUENCE: 6

Met Ala Gln Glu Phe Val Asn Cys Lys Ile Gln Ser Gly Lys Val Val
1               5                   10                  15

Val Phe Ile Lys Pro Thr Cys Pro Tyr Cys Arg Lys Thr Gln Glu Ile
            20                  25                  30

Leu Ser Gln Leu Pro Phe Lys Gln Gly Leu Leu Glu Phe Val Asp Ile
        35                  40                  45

Thr Ala Thr Asn Asn Thr Ser Ala Ile Gln Asp Tyr Leu Gln Gln Leu
    50                  55                  60

Thr Gly Ala Arg Thr Val Pro Arg Val Phe Ile Gly Lys Asp Cys Ile
65                  70                  75                  80

Gly Gly Cys Ser Asp Leu Ile Ser Met Gln Gln Thr Gly Glu Leu Met
                85                  90                  95

Thr Arg Leu Lys Gln Ile Gly Ala Leu Gln Leu
            100                 105

<210> SEQ ID NO 7
<211> LENGTH: 4
<212> TYPE: PRT
<213> ORGANISM: mus musculus

<400> SEQUENCE: 7

Asn Asn Thr Ser
1

<210> SEQ ID NO 8
<211> LENGTH: 17
<212> TYPE: PRT
<213> ORGANISM: mus musculus

<400> SEQUENCE: 8

Val Phe Ile Lys Pro Thr Cys Pro Tyr Cys Arg Lys Thr Gln Glu Ile
1               5                   10                  15

Leu

<210> SEQ ID NO 9
<211> LENGTH: 4
<212> TYPE: PRT
<213> ORGANISM: mus musculus

<400> SEQUENCE: 9

Glu Phe Val Asp
1
```

TREATMENTS INVOLVING GLUTAREDOXINS AND SIMILAR AGENTS

RELATED APPLICATIONS

This application is a national stage entry under 35 U.S.C. §371 of International Patent Application Serial No. PCT/US2008/007246, filed Jun. 10, 2008, entitled "Treatments Involving Glutaredoxins and Similar Agents," by Janssen-Heininger, et al., published as WO 2008/154012 on Dec. 18, 2008, which claims the benefit of U.S. Provisional Patent Application Ser. No. 60/934,129, filed Jun. 11, 2007, entitled "Treatments Involving Glutaredoxins and Similar Agents," by Janssen-Heininger, et al., each of which is incorporated herein by reference.

GOVERNMENT FUNDING

Research leading to various aspects of the present invention were sponsored, at least in part, by NIH RO1 HL60014, HL60812, Public Health Service P20 RL15557 (NCRR COBRE) and PO1 HL67004. The U.S. Government has certain rights in the invention.

FIELD OF INVENTION

The present invention generally relates to treatments and compositions comprising glutaredoxins.

BACKGROUND

Mammalian glutaredoxins (GRX) are members of the thiol-disulfide oxidoreductase family. They are often characterized by a thioredoxin fold and a Cys-Pro (Ser)-Tyr-Cys active site (SEQ ID NO:1). Examples include GRX1, a cytosolic protein, and GRX2, which may be directed to the mitochondria by a mitochondrial leader sequence and/or can also occur in the nucleus following alternative splicing. Mammalian glutaredoxins may specifically catalyze the reversible reduction of protein-glutathionyl-mixed disulfides to free sulfhydryl groups, using glutathione (GSH) as a cofactor.

SUMMARY OF THE INVENTION

The present invention generally relates to compositions and treatments involving glutaredoxins. The subject matter of the present invention involves, in some cases, interrelated products, alternative solutions to a particular problem, and/or a plurality of different uses of one or more systems and/or articles.

In some embodiments the invention provides compositions comprising glutaredoxins. In some embodiments of the composition comprising the glutaredoxin, the glutaredoxin has an inactivated caspase cleavage site. In some embodiments of the composition, the glutaredoxin is GRX1, GRX2, GRX5 or has a homology of greater than 90% with GRX1. In some embodiments of the composition the glutaredoxin active site comprises Cys-Pro-Tyr-Cys (SEQ ID NO:1), Cys-Ser-Tyr-Cys (SEQ ID NO:2) or Cys-Gly-Phe-Ser (SEQ ID NO:3). In some embodiments of the composition the glutaredoxin is a human glutaredoxin. In some embodiments of the composition the glutaredoxin is not human lens thioltransferase. In some embodiments the composition further comprises a pharmaceutically acceptable carrier. In some embodiments the composition further comprises an additional therapeutic compound. In some embodiments the therapeutic compound is a thioredoxin.

In some embodiments the invention provides compositions comprising a glutaredoxin in combination with a pharmaceutically acceptable carrier for pulmonary delivery, wherein glutaredoxin is GRX1, GRX2, GRX5, or a modified version thereof. In some embodiments the modified version of GRX1, GRX2 or GRX5 comprises an inactivated caspase cleavage site. In some embodiments the modified version of GRX1 has a homology of greater than 90% with unmodified GRX1. In some embodiments the glutaredoxin active site comprises Cys-Pro-Tyr-Cys (SEQ ID NO:1), Cys-Ser-Tyr-Cys (SEQ ID NO:2) or Cys-Gly-Phe-Ser (SEQ ID NO:3). In some embodiments the glutaredoxin is a human glutaredoxin. In some embodiments the composition further comprises an additional therapeutic compound. In some embodiments the additional therapeutic compound is a thioredoxin. In some embodiments the pharmaceutically acceptable carrier for pulmonary delivery is an aerosol formulation. In some embodiments the composition further comprises an inhaler, wherein the composition is contained in the inhaler.

In some embodiments the invention provides compositions comprising a human glutaredoxin formulated in a sterile pharmaceutically acceptable carrier suitable for administration to a human, wherein the human glutaredoxin is not human lens thioltransferase or GRX1. In some embodiments the pharmaceutically acceptable carrier is a topical formulation.

In some aspects the invention provides a method of promoting wound healing comprising administering a glutaredoxin to a subject having a wound. In some embodiments the glutaredoxin is administered directly to the wound. In some embodiments the glutaredoxin is administered topically. In some embodiments the glutaredoxin is administered systemically.

In some aspects the invention provides a method of treating cancer comprising administering to a subject having cancer an effective amount of glutaredoxin to treat the cancer.

In some aspects the invention provides a method of treating a cardiovascular disorder comprising administering to a subject having a cardiovascular disorder an effective amount of glutaredoxin to treat the cardiovascular disorder.

In some aspects the invention provides a method of treating a neurodegenerative disorder comprising administering to a subject having a neurodegenerative disorder an effective amount of glutaredoxin to treat the neurodegenerative disorder. In some embodiments the neurodegenerative disorder is not Alzheimer's disease or Parkinson's disease.

In some aspects the invention provides a method of treating pulmonary disease comprising administering to a subject having pulmonary disease an effective amount of glutaredoxin to treat the pulmonary disease. In some embodiments the pulmonary disease is ARDS In some aspects the invention provides a method of treating cystic fibrosis comprising administering to a subject having cystic fibrosis an effective amount of glutaredoxin to treat cystic fibrosis.

In some aspects the invention provides a method of treating asthma comprising administering to a subject having asthma an effective amount of glutaredoxin to treat asthma.

In some aspects the invention provides a method comprising administering, to a subject having or being at risk for a condition characterized by oxidative stress, a composition comprising glutaredoxin, wherein the glutaredoxin is GRX1, GRX2, GRX5 or a modified version thereof. In some embodiments the modified version of GRX1, GRX2, or GRX5 comprises an inactivated caspase cleavage site. In some embodiments the modified version of GRX1 has a homology of greater than 90% with unmodified GRX1. In some embodiments the glutaredoxin active site comprises Cys-Pro-Tyr-Cys (SEQ ID NO:1), Cys-Ser-Tyr-Cys (SEQ ID NO:2) or Cys-Gly-Phe-Ser (SEQ ID NO:3). In some embodiments the glutaredoxin is a human glutaredoxin. In some embodiments the method further comprises a pharmaceutically acceptable carrier. In some embodiments the pharmaceutically acceptable carrier is a carrier for pulmonary delivery. In some embodiments the glutaredoxin is administered by pulmonary delivery. In some embodiments the method further comprises administering an additional therapeutic compound. In some embodiments the additional therapeutic compound is a thioredoxin.

In some aspects the invention provides a kit comprising a container housing a glutaredoxin with a modified caspase cleavage site and instructions for administering components in the kit to a subject having or being at risk for a condition characterized by oxidative stress. In some embodiments the kit further comprises a container housing a pharmaceutical preparation diluent.

In some aspects the invention provides a kit comprising a container housing GRX1, GRX2, GRX5 or a modified version thereof and instructions for administering components in the kit to a subject having or being at risk for a condition characterized by oxidative stress. In some embodiments the kit further comprises a container housing a pharmaceutical preparation diluent.

In another aspect, the present invention is directed to a method of promoting one or more of the embodiments described herein.

Several methods are disclosed herein of administering to a subject a composition for treatment of a particular condition. It is to be understood that in each such aspect of the invention, the invention specifically includes, also, the composition for use in the treatment of that particular condition, as well as use of the composition for the manufacture of a medicament for the treatment of that particular condition.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 2A-2D illustrate cells exposed to GRX, in another embodiment of the invention;

FIGS. 5A-5J illustrate regulation of GRX1 and S-glutathionylation, in accordance with one embodiment of the invention;

FIG. 7 shows the protein structure of mouse GRX1 according to one embodiment of the invention;

DETAILED DESCRIPTION

Figure 1A:
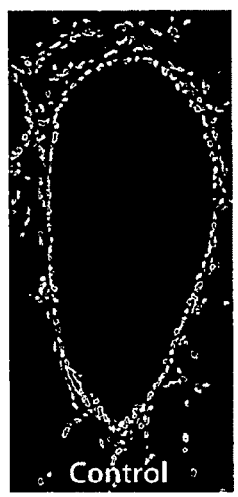
FIGS. 1A-1C illustrate reactivity in mice with allergic airways disease to ovalbumin, according to one embodiment of the invention.

The present invention generally relates to treatments, compositions and kits involving glutaredoxins. In some embodiments the glutaredoxins are modified to increase their in vivo protease resistance or processing. In some embodiments the caspase cleavage site of the glutaredoxins has been inactivated. In some embodiments the invention provides methods and kits for the treatment of diseases and conditions caused or characterized by oxidative stress through the administration of glutaredoxin.

It should be appreciated that the invention is described using glutaredoxin, but that the invention can be practiced with enzymes having the same biological activity.

Glutathione (GSH) represents a major low molecular weight antioxidant recycling thiol in mammalian cells and plays a central role in the cellular defense against oxidative damage. As part of its antioxidant properties, glutathione can conjugate with protein amino acid sulfhydryls through a thiol group to protect them directly against irreversible oxidations. Glutathione levels are regulated by a system of antioxidant enzymes that include glutathione peroxidases (GPx), glutathione reductase (GR), gamma-glutamyl-cysteinyl synthase (gamma-GCS), glutathione-S-transferase (GST), and glutaredoxins (GRX; also called thioltransferases). GRXs are oxidoreductases that can catalyze the reversible exchange of GSH with protein thiol groups. At high ratios of GSH/GSSG, as typically occur in physiological settings, the reduction of protein-glutathione mixed disulfides to restore the reduced sulfhydryl group is generally favored. This deglutathionylation reaction is believed to occur through a monothiol mechanism in which GRX itself is S-glutathionylated. The reduced state of GRX may be restored by GSH coupled to GSSG reductase.

During oxidative stress, oxidized glutathione levels (GSSG) may be increased as shown in BAL fluid or induced sputum samples of patients with asthma. In addition, higher levels of oxidative stress have been associated with an increased formation of mixed disulfides (also known as S-glutathionylation). Glutathionylation has been observed on a variety of proteins including the transcription factors NF-κB (NF kappa B), AP-1, and caspase-3 and glutathionylation can modify the biological function of these proteins.

In some aspects of the invention an oxidative stress condition may be treated using one or more compositions of the present invention. In some embodiments the oxidative stress condition in a subject may be treated by increasing the concentration of glutathione systemically or in the area affected by the oxidative stress. Without wishing to be bound by any theory, it is believed that glutaredoxin can cause a decrease in protein glutathionylation (mixed disulfides), thereby alleviating the effects oxidative stress. Prior to the instant invention it was unknown whether exogenously administered glutaredoxins would be sufficient to overcome damage associated with oxidative stress to a degree such that it would be useful for treating disease. As shown in the examples it has now been demonstrated in vivo that glutaredoxins are an important component in the antioxidant defense system in diseases such as allergy and asthma. Cells experiencing oxidative stress may show increases in protein glutathionylation, and higher reactivities and/or sensitivities to foreign agents and the like. Accordingly, by administering glutaredoxin, oxidative stress conditions such as airway inflammation or asthma may be treated by causing decreased protein glutathionylation in such cells, and a corresponding decrease in reactivity and/or sensitivity to foreign agents. In addition, the administration of glutaredoxin may ultimately lead to an increase in the level of the antioxidant glutathione, and protect proteins against irreversible oxidations.

Various aspects of the present invention relate to oxidized proteins and glutathionylated proteins. An "oxidized" protein, as used herein, is a protein in which at least one (native) amino acid residue of the protein has been oxidized in some fashion. As an example, glutathione may react with a residue on the protein to glutathionylate the residue. Thus, as used herein, a "glutathionylated" protein is a protein in which at least one amino acid residue of the protein has been glutathionylated, i.e., the amino acid residue has reacted with glutathione, typically through the addition of the glutathione (or a portion thereof) to the residue. Residues that may undergo reactions with glutathione include sulfhydryl moieties (—SH) (e.g., from a cysteine residue), hydroxyl moieties (—OH) (e.g., from a serine residue or a threonine residue), or the like. As a particular example, if the residue includes a sulfhydryl moiety (—SH) (also referred to as a thiol moiety), reaction of the moiety with glutathione can produce an S-glutathionylated moiety, i.e., —S—S-G, where "G" represents glutathione). The "S-" signifies reaction with the sulfhydryl moiety. In some cases, "S-glutathionylation" is also called "S-glutathiolation."

Thus, the invention relates, in some aspects, to a method of treating a condition characterized by oxidative stress. A condition characterized by oxidative stress is one in which oxidative stress plays a role in the development of the disease or one or more symptoms of the disease. In a subject, an oxidative stress condition may be caused by certain types of chronic diseases or conditions, for example, airway inflammation, Acute Respiratory Distress Syndrome (ARDS), aging, asthmas, emphysema, cancers, rheumatoid arthritis, atherosclerosis, alcohol addition, certain types of cardiovascular disease, certain types of chronic inflammatory diseases, or certain types of neurodegenerative diseases, such as Lou Gehrig's Disease, Parkinson's Disease, Alzheimer's Disease, sporadic amytrophic lateral sclerosis, or Huntington's Disease. Such diseases are often characterized by chronic altered metabolic states in which there are elevated concentrations of certain reactive oxygen species, such as superoxides, singlet oxygens, peroxynitrite, ozone, or hydrogen peroxide. In some embodiments the higher levels or oxidants are caused by inflammation, for instance through the activity of macrophages. In some cases, the reactive oxygen species are created by external factors, such as radiation or ultraviolet light. Other agents that may lead to oxidized proteins include, but are not limited to, chemical reagents such as hydrogen peroxide, $NO_x$ species, or the like, or certain types of biological reactions, such as enzymes that produce oxidative intermediate species (e.g., metabolic enzymes).

The lungs are constantly being exposed to oxygen and are susceptible to oxidative stress. Oxidative stress conditions that can be treated using the present invention include pulmonary diseases such as COPD (chronic obstructive pulmonary disease, also known as chronic obstructive airway disease, which includes chronic bronchitis and/or emphysema), ARDS (acute respiratory distress syndrome), including pulmonary edema, bronchopulmonary dysplasia (BPD), asthma and cystic fibrosis.

Asthma refers to a disorder of the respiratory system characterized by inflammation, narrowing of the airways, and/or increased reactivity of the airways to inhaled agents. Asthma is frequently, although not exclusively, associated with atopic or allergic symptoms. As used herein, a subject having asthma includes those subjects that have been identified as having asthma but that do not have the active disease during the therapy of the invention, as well as subjects that have the active disease of asthma. The airways of asthmatic subjects have elevated levels of Th2 cytokines, especially IL-4 and IL-5. These cytokines promote important aspects of the asthmatic inflammatory response, including IgE isotype switching, eosinophil chemotaxis and activation and mast cell growth. Th1 cytokines, especially IFN-γ (IFN-gamma) and IL-12, can suppress the formation of Th2 clones and production of Th2 cytokines.

Chronic obstructive pulmonary disease (COPD) is used to describe two conditions of fixed airways disease, chronic bronchitis and emphysema. Chronic bronchitis and emphysema are most commonly caused by smoking. COPD is generally characterized by having limited airflow in the lungs and/or a rapid breathing rate, as well as wheezing in the lungs. Emphysema is characterized by destruction of alveolar walls leading to abnormal enlargement of the air spaces of the lung. Chronic bronchitis is defined clinically as the presence of chronic productive cough for three months in each of two successive years. In COPD, airflow obstruction is usually progressive and is only partially reversible. The airflow obstruction associated with COPD is progressive, may be accompanied by airway hyperreactivity.

Chronic inflammation of the airways is a key pathological feature of COPD. The inflammatory cell population comprises increased numbers of macrophages, neutrophils, and CD8+ lymphocytes. Inhaled irritants, such as cigarette smoke, activate macrophages which are resident in the respiratory tract, as well as epithelial cells leading to release of chemokines (e.g., interleukin-8) and other chemotactic factors. These chemotactic factors act to increase the neutrophil/monocyte trafficking from the blood into the lung tissue and airways. Neutrophils and monocytes recruited into the airways can release a variety of potentially damaging mediators such as proteolytic enzymes and reactive oxygen species. Matrix degradation and emphysema, along with airway wall thickening, surfactant dysfunction, and mucus hypersecretion, all are potential sequelae of this inflammatory response that lead to impaired airflow and gas exchange.

A broad range of immune and inflammatory cells including neutrophils, macrophages, T lymphocytes and eosinophils contain proteolytic enzymes that could contribute to the destruction of lung extracellular matrix (Shapiro, 1999). In addition, a number of different classes of proteases have been identified that have the potential to contribute to lung matrix destruction. These include serine proteases, matrix metalloproteinases and cysteine proteases. Of these classes of enzymes, a number can hydrolyze elastin and have been shown to be elevated in COPD patients (neutrophil elastase, MMP-2, 9, 12) (Culpitt et al., Am. J. Respir. Crit. Care Med. 160, 1635 39, 1999, Shapiro, Am. J. Crit. Care Med. 160 (5), S29 S32, 1999).

Adult Respiratory Distress Syndrome (ARDS) is a disease of a large number of acute, diffusely infiltrative pulmonary lesions of different etiology if they are associated with a severe gas exchange disorder (in particular arterial hypoxemia). ARDS is generally characterized by inflammation of the lungs which leads to impaired breathing. ARDS can be identified using bilateral infiltrates on chest radiograph, and/or measurements of the partial pressure of oxygen in the lungs and/or the fraction of inspired oxygen.

Triggering causes for ARDS can, for example, be (cited in accordance with Harrison's Principles of Internal Medicine 10th Ed. 1983 McGraw-Hill Int. Book Comp.) diffuse pulmonary infections (for example due to viruses, bacteria, fungi), aspiration of, for example, gastric juice or in the case of near-drowning, inhalation of toxins or irritants (for example chlorine gas, nitrogen oxides, smoke), direct or indirect trauma (for example multiple fractures or pulmonary contusion), systemic reactions to inflammations outside the lung (for example hemorrhagic pancreatitis, gram-negative septicemia), transfusions of high blood volumes or alternatively after cardiopulmonary bypass.

The therapy of ARDS consists mainly in the earliest possible application of different forms of ventilation [for example PEEP (positive end-expiratory pressure), raising of the oxygen concentration of the respiratory air, SIMV (Synchronized Intermittent Mandatory Ventilation; Harrison's Principles of Internal Medicine 10th Ed. 1983 McGraw-Hill Int. Book Comp.)] up to extracorporeal membrane oxygenation (ECMO; Zapol and Lemaire Adult Respiratory Distress Syndrome, Marcel Dekker Inc, 1991).

Bronchopulmonary Dysplasia (BPD) refers to a chronic lung disease that can develop in preterm neonates treated with oxygen and positive-pressure ventilation. BPD results from a variety of factors, including oxidative stress, that can injure small airways and that can interfere with alveolarization (septation), leading to alveolar simplification with a reduction in the overall surface area for gas exchange.

Cystic fibrosis is caused by a mutation in a protein called the cystic fibrosis transmembrane conductance regulator (CFTR). Changes in GSH metabolism have been associated with cystic fibrosis, as the CFTR transporter is regulated by S-glutathionylation. Cystic fibrosis is the most common severe autosomal recessive genetic disorder in the Caucasian population. It affects approximately 1 in 2000 live births in North America [Boat et al, The Metabolic Basis of Inherited Disease, 6th ed, pp 2649-2680, McGraw Hill, NY (1989)]. Approximately 1 in 20 persons are carriers of the disease. The major symptoms of cystic fibrosis include chronic pulmonary disease, pancreatic exocrine insufficiency, and elevated sweat electrolyte levels.

Cystic fibrosis (CF) is an autosomal recessive disease characterized by disturbances in ion transport and viscous epithelial mucous secretions. The CF gene protein, CFTR acts as a Cl-channel and is also a key regulator of protein secretion.

Oxidative stress is believed to be a causative or at least ancillary factor in the pathogenesis of major neurodegenerative diseases and aging. In some embodiments the invention is directed to treating a neurodegenerative disease with glutaredoxin. In some cases the invention contemplates the treatment of subjects having neurodegenerative disease, or an injury to nerve cells which may lead to neuro-degeneration. Neuronal cells are predominantly categorized based on their local/regional synaptic connections (e.g., local circuit interneurons vs. longrange projection neurons) and receptor sets, and associated second messenger systems. Neuronal cells include both central nervous system (CNS) neurons and peripheral nervous system (PNS) neurons. There are many different neuronal cell types. Examples include, but are not limited to, sensory and sympathetic neurons, cholinergic neurons, dorsal root ganglion neurons, proprioceptive neurons (in the trigeminal mesencephalic nucleus), ciliary ganglion neurons (in the parasympathetic nervous system), etc. A person of ordinary skill in the art will be able to easily identify neuronal cells and distinguish them from non-neuronal cells such as glial cells, typically utilizing cell-morphological characteristics, expression of cell-specific markers, secretion of certain molecules, etc.

"Neurodegenerative disorder" or "neurodegenerative disease" is defined herein as a disorder in which progressive loss of neurons occurs either in the peripheral nervous system or in the central nervous system. Non-limiting examples of neurodegenerative disorders include: (i) chronic neurodegenerative diseases such as familial and sporadic amyotrophic lateral sclerosis (FALS and ALS, respectively), familial and sporadic Parkinson's disease, Huntington's disease, familial and sporadic Alzheimer's disease, multiple sclerosis, olivopontocerebellar atrophy, multiple system atrophy, progressive supranuclear palsy, diffuse Lewy body disease, corticodentatonigral degeneration, progressive familial myoclonic epilepsy, strionigral degeneration, torsion dystonia, familial tremor, Down's Syndrome, Gilles de la Tourette syndrome, Hallervorden-Spatz disease, diabetic peripheral neuropathy, dementia pugilistica, AIDS Dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapie, and kuru), and those caused by excess cystatin C accumulation (hereditary cystatin C angiopathy); and (ii) acute neurodegenerative disorders such as traumatic brain injury (e.g., surgery-related brain injury), cerebral edema, peripheral nerve damage, spinal cord injury, Leigh's disease, Guillain-Barre syndrome, lysosomal storage disorders such as lipofuscinosis, Alper's disease, vertigo as result of CNS degeneration; pathologies arising with chronic alcohol or drug abuse including, for example, the degeneration of neurons in locus coeruleus and cerebellum; pathologies arising with aging including degeneration of cerebellar neurons and cortical neurons leading to cognitive and motor impairments; and pathologies arising with chronic amphetamine abuse including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor), and Wernicke-Korsakoff's related dementia. Neurodegenerative diseases affecting sensory neurons include Friedreich's ataxia, diabetes, peripheral neuropathy, and retinal neuronal degeneration. Neurodegenerative diseases of limbic and cortical systems include cerebral amyloidosis, Pick's atrophy, and Retts syndrome. The foregoing examples are not meant to be comprehensive but serve merely as an illustration of the term "neurodegenerative disorder or "neurodegenerative disease". In some embodiments the treatment of neurodegenerative disease includes the treatment of Alzheimer's and Parkinson's diseases and in other embodiments the treatment of the disease is excluded.

Most of the chronic neurodegenerative diseases are typified by onset during the middle adult years and lead to rapid degeneration of specific subsets of neurons within the neural system, ultimately resulting in premature death. Compositions comprising glutaredoxin may be administered to a subject to treat neurodegenerative disease alone or in combination with the administration of other therapeutic compounds for the treatment or prevention of these disorders or diseases. Many of these drugs are known in the art. For example, antiparkinsonian agents include but are not limited to Benztropine Mesylate; Biperiden; Biperiden Hydrochloride; Biperiden Lactate; Carmantadine; Ciladopa Hydrochloride; Dopamantine; Ethopropazine Hydrochloride; Lazabemide; Levodopa; Lometraline Hydrochloride; Mofegiline Hydrochloride; Naxagolide Hydrochloride; Pareptide Sulfate; Procyclidine Hydrochloride; Quinelorane Hydrochloride; Ropinirole Hydrochloride; Selegiline Hydrochloride; Tolcapone; Trihexyphenidyl Hydrochloride. Drugs for the treatment of amyotrophic lateral sclerosis include but are not limited to Riluzole. Drugs for the treatment of Paget's disease include but are not limited to Tiludronate Disodium.

Proliferative diseases are characterized by uncontrolled cell growth. Oxidative stress has been associated with proliferative diseases, mostly because of its role in oxidizing proteins and other cellular components, thereby modulating cell signaling and cell growth. In some embodiments the compositions of the present invention can be used to treat proliferative diseases including cancer. "Cancer" as used herein refers to an uncontrolled growth of cells which interferes with the normal functioning of the bodily organs and systems. Cancers which migrate from their original location and seed vital organs can eventually lead to the death of the subject through the functional deterioration of the affected organs. Hemopoietic cancers, such as leukemia, are able to outcompete the normal hemopoietic compartments in a subject, thereby leading to hemopoietic failure (in the form of anemia, thrombocytopenia and neutropenia) ultimately causing death. Many tumors have altered metabolic demand, including oxidative stresses, and such altered antioxidant defenses may permit tumor growth. Such effects may be countered, at least in part, by the application of the compositions discussed herein comprising a glutaredoxin. Examples of cancers that can be treated using the compositions of the invention include, but are not limited to: biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma, teratomas, choriocarcinomas; stromal tumors and germ cell tumors; thyroid cancer including thyroid adenocarcinoma and medullar carcinoma; and renal cancer including adenocarcinoma and Wilms' tumor. Commonly encountered cancers include breast, prostate, lung, ovarian, colorectal, and brain cancer. In general, an effective amount of the one or more compositions of the invention for treating cancer will be that amount necessary to inhibit mammalian cancer cell proliferation in situ. Those of ordinary skill in the art are well-schooled in the art of evaluating effective amounts of anti-cancer agents.

In some embodiments treatment methods of the invention may be combined with known cancer treatment methods. The term "cancer treatment" as used herein, may include, but is not limited to, chemotherapy, immunotherapy, radiotherapy, adjuvant therapy, surgery, or any combination of these and/or other methods. Particular forms of cancer treatment may vary, for instance, depending on the subject being treated. Examples include, but are not limited to, dosages, timing of administration, duration of treatment, etc. One of ordinary skill in the medical arts can determine an appropriate cancer treatment for a subject.

In some embodiments the cancer medicament is a chemotherapeutic agent selected from the group consisting of methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS famesyl transferase inhibitor, famesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Placlitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCI, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bisguanylhydrazone; MGBG), Pentostatin (2'deoxycoformycin), Semustine (methyl-CCNU), Teniposide (VM-26) and Vindesine sulfate. In some embodiments the cancer medicament is taxol.

In some embodiments the cancer medicament is an immunotherapeutic agent selected from the group consisting of Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab and ImmuRAIT-CEA.

The heart is one of the most prominent oxygen-consuming organs and oxidative stress is associated with cardiovascular diseases and heart failures. "Cardiovascular disorders" include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, congestive heart failure, coronary artery disease, valvular disease, arrhythmias, and cardiomyopathies. Other disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, artherosclerosis, and hypertensive vascular disease; inflammatory disease—the vasculitides, such as giant cell (temporal) arteritis, Takayasu arterisis, polyarterisis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

In another aspect, the methods of the invention are useful in treating wounds in subjects. As used herein, the term "wound" is used to describe skin wounds as well as tissue wounds. A "skin wound" is defined herein as a break in the continuity of skin tissue which is caused by direct injury to the skin. Skin wounds are generally characterized by several classes including punctures, incisions, including those produced by surgical procedures, excisions, lacerations, abrasions, atrophic skin, or necrotic wounds and burns. The methods of the invention are useful for enhancing or promoting the healing of all wounds of the skin.

A "tissue wound," as used herein, is a wound to an internal organ, such as a blood vessel, intestine, colon, etc. The methods of the invention are useful for enhancing the wound healing process in tissue wounds, whether they arise naturally, or as the result of surgery. For instance, during the repair of arteries an artery may need to be sealed and wound healing promoted as quickly as possible. The methods of the invention may speed up or otherwise enhance that process.

In the method of promoting wound healing the compounds of the invention may be applied directly to the wound unformulated or in a carrier such as a topical liquid, lotion or cream or in any pharmaceutical formulation such as a microcarrier. The compounds may also be attached to a bandage or other substrate, and the substrate positioned over a wound, to completely or at least partially cover the wound. In some cases the bandage or other substrate may be adhered to the subject, for example, through the use of adhesives. Suitable adhesives can be selected by those of ordinary skill in the art.

The compounds of the invention may also be administered with additional therapeutic and/or pharmacologically acceptable agents. For instance, the compositions or methods may involve other agents for the treatment of wounds such as, for instance, dexpanthenol, growth factors, enzymes or hormones, povidon-iodide, fatty acids, such as cetylphridinium chloride, antibiotics, and analgesics. In some embodiments, the compositions may also include growth factors. Growth factors include, but are not limited to, fibroblast growth factor (FGF), FGF-1, FGF-2, FGF-4, platelet-derived growth factor (PDGF), insulin-binding growth factor (IGF), IGF-1, IGF-2, epidermal growth factor (EGF), transforming growth factor (TGF), TGF-alpha, TGF-beta, cartilage inducing factors –A and –B, osteoid-inducing factors, osteogenin and other bone growth factors, collagen growth factors, heparin-binding growth factor –1 or –2, and/or their biologically active derivatives. The compositions may also include antiseptics in some embodiments.

In one embodiment, the oxidative stress condition may be diagnosed within a subject by providing a sample taken from the subject (e.g., a blood sample, cells, fluid, etc.), exposing the sample to a reducing agent, such as an enzyme, able to interact with certain proteins within the sample (e.g., an enzyme or other reducing agent able to react with glutathione or nitroso groups on the protein), and determining if the proteins have been oxidized and in some cases, to what degree.

Other methods of diagnosing an oxidative stress condition are known in the art and include, determining the presence of reactive oxygen species in a subject or sample taken from a subject, wherein reactive oxygen species include singlet oxygen, nitric oxide, superoxide, hydroxy peroxide and peroxynitrite. Oxidative stress may also be diagnosed by determining the presence of oxidized elements in a subject or sample taken from a subject, wherein oxidized elements include oxidized proteins, lipids and nucleic acids. Based on the results of this assay, the subject may be diagnosed as having an oxidative stress condition, which may be indicative of certain diseases, as previously described. The diagnosis of oxidative stress in a subject may be a factor in the decision to initiate the treatment methods of the current invention. Examples of suitable methods of diagnosing an oxidative stress condition are disclosed in U.S. Provisional Patent Application Ser. No. 60/761,956, filed Jan. 25, 2006, entitled "Detection of Glutathionylated Proteins," by Y. Janssen-Heininger; U.S. Provisional Patent Application Ser. No. 60/774,060, filed Feb. 16, 2006, entitled "Detection of Glutathionylated Proteins," by Y. Janssen-Heininger; and U.S. patent application Ser. No. 11/698,300 filed on Jan. 25, 2007, entitled "Detection of Glutathionylated Proteins," by Y. Janssen-Heininger, each of which is incorporated herein by reference.

The therapeutic compounds useful according to the invention are glutaredoxins. Glutaredoxins belong to a family of compounds referred to as disulfide reductases. Disulfide reductases are enzymes that reduce disulfide bonds. Examples of disulfide reductases are glutaredoxin (also called thioltransferase; e.g. Johansson et al., 2004, JBC 279: 7357-7543), thioredoxin (e.g., Watson et al., 2004, Toxicological Sci. 78: 3-14), flavoprotein reductases (e.g., Argyrou et al. 2004, Prog Nucleic Acid Res Mol Biol 78: 89-142), and the Dsb protein family (e.g., Chivers et al. 1997, Biochemistry 36: 4061-4060), ResA and CcdA (e.g. Erlendsson et al. 2003, JBC 278: 17582-17858).

Glutaredoxin and thioredoxin are disulfide reductases involved in maintaining cellular thiolredox homeostasis. Glutaredoxins and thioredoxins comprise the family of thiol-didulfide oxidoreductases that are characterized by the thioredoxin fold. Both enzymes catalyze the reversible reduction of protein disulfides. The term glutaredoxin, as used herein, refers to a peptide or nucleic acid encoding a peptide that has at least 80% and more preferably at least 90% homology with a native glutaredoxin peptide or nucleic acid respectively and which maintains at least one biological function of glutaredoxin, even if the potency is less than native glutaredoxin. In some embodiments the potency of the glutaredoxin is at least 50%, 60%, 70%, 80%, 90%, 95% or preferably 98% or greater of native glutaredoxin. A native glutaredoxin is any naturally occurring glutaredoxin.

The glutaredoxins of the invention include mammalian glutaredoxins, such a human as well as other organisms. Mammalian glutaredoxins include GRX1, a cytosolic protein with active site Cys-Pro-Tyr-Cys (SEQ ID NO:1), and GRX2 with active site Cys-Ser-Tyr-Cys (SEQ ID NO:2), which may be directed to the mitochondria by a mitochondrial leader sequence and/or can also occur in the nucleus following alternative splicing and GRX5 a mitochondrial glutaredoxin, named GRX5 because it is homologous to yeast CRX5, with only one Cys residue in it active site, Cys-Gly-Phe-Ser (SEQ ID NO:3) (Wingert et al., 2005, Nature 436: 1035-1039). In addition, a human lens thioltransferase has been reported (U.S. Pat. No. 6,379,664) with 87% homology to human GRX1 and having Cys-Pro-Phe-Cys (SEQ ID NO:4) as active site.

Mammalian thioredoxins include the cytosolic TRX1 and the mitochondrial TRX2, both comprising a Gly-Cys-SeCys-Gly (SEQ ID NO:5) active site. TRX1 is involved in the redox regulation of a variety of proteins including transcription factors (for instance NF-κB subunit p50) and proteins involved in the regulation of apoptosis (like ASK-1).

Many glutaredoxins are available commercially. For example, GRXs derived from humans or *E. coli* can be obtained from Imco Crop. (Sweden, distributed by American Diagnostica, Stamford, Conn.), or in some cases, glutaredoxins can be prepared recombinantly using methods known to those of ordinary skill in the art or synthetically. The sequences of several known glutaredoxins are presented in the Sequence Listing.

A modified protein relates to a protein that comprises one or more modifications, including amino acid substitutions, polypeptide backbone modifications, amino acid side chain modifications, and modifications at the N- or C-terminus. Modifications include changes that render proteins more stable and/or more resistant towards proteases or other processing enzymes. These modifications include amino acids substitutions or deletions that stabilize secondary structure, which can be achieved, for instance, by resulting in shortened secondary structure loops, and substitutions that make proteins less resistant towards proteases include, which can be achieved, for instance, by minimizing the number of amino acids that are most readily cleaved by proteases. All modified glutaredoxins are embraced by the invention.

As demonstrated in the Examples, glutaredoxins have a putative caspase cleavage site which has been shown to be cleaved by caspases in vitro. Modified glutaredoxins include glutaredoxins that have a modified caspase cleavage site. In some embodiments the caspase cleavage site is modified to prevent the site form being cleaved by caspases referred to herein as an inactivated caspase cleavage site. Glutaredoxins with an inactivated caspase cleavage site are particularly embraced by the invention. While all protein modifications are embraced by the invention, it is preferred that the modified glutaredoxin remains biologically active, i.e., can reduce protein disulfides. Compositions and methods comprising a biologically active portion of a glutaredoxin are also embraced by the invention.

A modified glutaredoxin having at least one substitution, deletion or insertion is also useful according to the invention. In some embodiments the glutaredoxin is a glutaredoxin having at least one conservative amino acid substitution from a native glutaredoxin. As used herein, a "conservative amino acid substitution" or "conservative substitution" refers to an amino acid substitution in which the substituted amino acid residue is of similar charge as the replaced residue and is of similar or smaller size than the replaced residue. Typically, the amino acid substitution which does not alter the relative charge or size characteristics of the protein in which the amino acid substitution is made. Such alterations can be prepared according to methods for altering peptide sequence known to one of ordinary skill in the art such as are found in references which compile such methods, e.g. *Molecular Cloning: A Laboratory Manual*, J. Sambrook, et al., Eds., Second Edition, Cold Spring Harbor Laboratory Press, Cold Spring Harbor, N.Y., 1989, or *Current Protocols in Molecular Biology*, F. M. Ausubel, et al., Eds., John Wiley & Sons, Inc., New York. Conservative substitutions of amino acids include substitutions made amongst amino acids within the following groups (using standard amino acid abbreviations): (a) the small non-polar amino acids, A, M, I, L, and V; (b) the small polar amino acids, G, S, T and C; (c) the amido amino acids, Q and N; (d) the aromatic amino acids, F, Y and W; (e) the basic amino acids, K, R and H; and (f) the acidic amino acids, E and D. Substitutions which are charge neutral and which replace a residue with a smaller residue may also be considered "conservative substitutions" even if the residues are in different groups (e.g., replacement of phenylalanine with the smaller isoleucine). The term "conservative amino acid substitution" also refers to the use of amino acid analogs or variants. In some embodiments the glutaredoxin has at least 2, 3, 4, 5, 6, 7, 8, 9, 10, 12, 13, 14, 15, 16, 17, 18, 19 or 20 conservative amino acid substitutions.

Methods for making amino acid substitutions, additions or deletions are well known in the art. The terms "conservative substitution," "non-conservative substitutions," "non-polar amino acids," "polar amino acids," and "acidic amino acids" are all used consistently with the prior art terminology. Each of these terms is well-known in the art and has been extensively described in numerous publications, including standard biochemistry text books, such as *Biochemistry* by Geoffrey Zubay, Addison-Wesley Publishing Co., 1986 edition, which describes conservative and non-conservative substitutions and properties of amino acids which lead to their definition as polar, non-polar or acidic. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding the glutaredoxin. The activity of functionally equivalent fragments of the glutaredoxin can be tested by cloning the gene encoding the altered enzyme into a bacterial or mammalian expression vector, introducing the vector into an appropriate host cell, expressing the enzyme, and testing for a functional capability of the enzyme as disclosed herein.

Substituting one or more amino acid leads to a modified glutaredoxin that has a certain percentage homology with the native enzyme. Homology is defined as the percentage of amino acids that is the same when a first variant of a glutaredoxin is compared to a second variant of the same enzyme. For instance, if one 1 out of 100 amino acids is different between the two variants than the variants are said to be 99% homologous. Analogously, if 2 out of 100 amino acids are substituted the amino acid is said to be 98% homologous. The invention embraces modified glutoredoxins that are more than 50%, more than 60%, more than 70%, more than 80%, more than 90%, and all values in between, up top 100% homologous to native glutaredoxin.

The modified glutaredoxin having at least one substitution, deletion or insertion may have, in some embodiments, a native conformation. A native conformation as used herein refers to a tertiary structure that is similar to the tertiary structure of native glutaredoxin domain. The tertiary structure of modified or native glutaredoxin domains can be assessed using structural analysis such as crystallography or by functional analysis, such as binding and/or activity assays and NMR spectroscopy.

The glutaredoxin may be delivered directly to cells in vitro or to a subject in vivo as a peptide or in a nucleic acid vector which will express the peptide in vivo. The enzyme, when delivered in vivo, may be isolated. As used herein, "isolated" means separate from its native environment. Isolated, when referring to a protein or peptide, means, for example: (i) selectively produced by expression cloning or (ii) purified as by chromatography or electrophoresis. Isolated proteins or peptides may, but need not be, substantially pure. The term "substantially pure" means that the proteins or peptides are essentially free of other substances with which they may be found in nature or in vivo systems to an extent practical and appropriate for their intended use. Substantially pure peptides may be produced by techniques well known in the art. Because an isolated protein may be admixed with a pharmaceutically acceptable carrier in a pharmaceutical preparation, the peptide may comprise only a small percentage by weight of the preparation. The peptide is nonetheless isolated in that it has been separated from the substances with which it may be associated in living systems, i.e. isolated from other peptides.

The invention also embraces nucleic acids encoding glutaredoxin and modified versions thereof. In some embodiments a nucleic acid encoding the enzyme is administered to a subject. In some embodiments an mRNA encoding the enzyme is administered to a subject. In some embodiments an isolated nucleic acid is administered to a subject. This method requires a polynucleotide which codes for a glutaredoxin operatively linked to a promoter and any other genetic elements necessary for the expression of the polypeptide by the target tissue.

In some embodiments the nucleic acid encoding the glutaredoxin is an integral part of a vector. As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids and viruses. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Preferred vectors are those capable of autonomous replication and expression of the structural gene products present in the DNA segments to which they are operably joined. Additional elements may also be needed for optimal synthesis of the mRNA coding for glutaredoxin. These elements may include splice signals, as well as transcription promoters, enhancers, and termination signals. cDNA expression vectors incorporating such elements include those described by Okayama (1983, Molec. Cell. Biol. 3, 280).

In some embodiments, the glutaredoxin polynucleotide (i.e. the nucleic acid encoding a glutaredoxin) is delivered as a naked polynucleotide. The term "naked" polynucleotide, DNA or RNA refers to sequences that are free from any delivery vehicle that acts to assist, promote or facilitate entry into the cell. For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The naked polynucleotides are delivered by any method known in the art, including, but not limited to, direct needle injection at the delivery site, intravenous injection, topical administration, catheter infusion, and so-called "gene guns".

The nucleic acids encoding a glutaredoxin may also be delivered with delivery vehicles such as viral sequences, viral particles, liposome formulations, lipofectin, precipitating agents, etc. In certain embodiments, a retroviral particle containing RNA which comprises a sequence encoding a glutaredoxin may be used. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus. Adenoviruses also can be manipulated such that it encodes and expresses the enzyme, and at the same time is inactivated in terms of its ability to replicate in a normal lytic viral life cycle. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells.

Any composition of the present invention may be administered to a subject, either by itself and/or in conjunction with co-factors, other therapeutics, or the like. For example, glutaredoxin may be administered alone, or in conjunction with co-factors such as GSSG reductase, GSH, or NADPH. When administered, the compositions of the invention can be applied in a therapeutically effective, pharmaceutically acceptable amount as a pharmaceutically acceptable formulation, for example, a pharmaceutically acceptable carrier such as those described below. The term "effective amount" of a composition, such as the enzymes of the invention, refers to the amount necessary or sufficient to realize a desired biologic effect. For example, an effective amount of a glutaredoxin to treat asthma is that amount sufficient to reduce or prevent further induction of Th2 cytokines in order to avoid exacerbation of asthma. Combined with the teachings provided herein, by choosing among the various active compositions and weighing factors such as potency, relative bioavailability, patient body weight, severity of adverse side effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular composition being administered the size of the subject, or the severity of the disease or condition. One of ordinary skill in the art can empirically determine the effective amount of a particular composition and/or other therapeutic agent without necessitating undue experimentation.

The terms "treat," "treated," "treating," and the like, when used herein with respect to a condition characterized by an oxidative stress condition, such as asthma, refer to administration of the compositions to a subject which may increase the resistance of the subject to development or further development of the condition, to administration of the composition after the subject has developed the condition in order to eliminate or at least control development of the condition, and/or slow the progression of or to reduce the severity of symptoms caused by the condition. When administered to a subject, effective amounts will depend on the particular condition being treated and the desired outcome. A therapeutically effective dose may be determined by those of ordinary skill in the art, for instance, employing factors such as those further described below and using no more than routine experimentation.

For use in therapy, an effective amount of the compositions of the present invention can be administered to a subject by any mode that delivers the composition to the desired surface, e.g., mucosal, systemic. Administering the pharmaceutical composition of the present invention may be accomplished by any means known to the skilled artisan. Preferred routes of administration include but are not limited to oral, parenteral, intramuscular, intranasal, sublingual, intratracheal, inhalation, ocular, vaginal, intravenously, percutaneously, and rectal.

In administering the compositions of the invention to a subject, dosing amounts, dosing schedules, routes of administration, and the like may be selected so as to affect known activities of these compositions. Dosages may be estimated based on the results of experimental models, optionally in combination with the results of assays of compositions of the present invention. Dosage may be adjusted appropriately to achieve desired drug levels, local or systemic, depending upon the mode of administration. The doses may be given in one or several administrations per day. Multiple doses per day are also contemplated in some cases to achieve appropriate systemic levels of the composition within the subject or within the active site of the subject.

The dose of the composition to the subject may be such that a therapeutically effective amount of the composition reaches an active site of the composition within the subject. The dosage may be given in some cases at the maximum amount while avoiding or minimizing any potentially detrimental side effects within the subject. The dosage of the composition that is actually administered is dependent upon factors such as the final concentration desired at the active site, the method of administration to the subject, the efficacy of the composition, the longevity of the composition within the subject, the timing of administration, the effect of concurrent treatments (e.g., as in a cocktail), etc. The dose delivered may also depend on conditions associated with the subject, and can vary from subject to subject in some cases. For example, the age, sex, weight, size, environment, physical conditions, or current state of health of the subject may also influence the dose required and/or the concentration of the composition at the active site. Variations in dosing may occur between different individuals or even within the same individual on different days. It may be preferred that a maximum dose be used, that is, the highest safe dose according to sound medical judgment. Preferably, the dosage form is such that it does not substantially deleteriously affect the subject.

Subject doses of the compounds described herein for mucosal or local delivery typically range from about 0.1 microgram to 10 mg per administration, which depending on the application could be given daily, weekly, or monthly and any other amount of time therebetween. More typically mucosal or local doses range from about 10 microgram to 5 mg per administration, and most typically from about 100 microgram to 1 mg, with 2 to 4 administrations being spaced days or weeks apart. More typically, doses range from 1 microgram to 10 mg per administration, and most typically 10 microgram to 1 mg, with daily or weekly administrations. Subject doses of the compounds described herein for parenteral delivery for the purpose of treating asthma may be typically 5 to 10,000 times higher than the effective mucosal dose, and more typically 10 to 1,000 times higher, and most typically 20 to 100 times higher. More typically parenteral doses for these purposes range from about 10 microgram to 5 mg per administration, and most typically from about 100 microgram to 1 mg, with 2 to 4 administrations being spaced days or weeks apart. In some embodiments, however, parenteral doses for these purposes may be used in a range of 5 to 10,000 times higher than the typical doses described above. The compositions of the present invention may be administered in multiple doses over extended period of time. For any compound described herein the therapeutically effective amount can be initially determined from animal models. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The treatments disclosed herein may be given to any subject, for example, a human, or a non-human animal, such as a dog, a cat, a horse, a rabbit, a cow, a pig, a sheep, a goat, a rat (e.g., *Rattus Norvegicus*), a mouse (e.g., *Mus musculus*), a guinea pig, a non-human primate (e.g., a monkey, a chimpanzee, a baboon, an ape, a gorilla, etc.), or the like. In one embodiment, the treatment is applied to cells, for example, cells taken from a human subject.

In certain embodiments, a composition of the invention is administered to a subject who has a family history of a condition characterized by an oxidative stress condition, such as asthma, or to a subject who has a genetic predisposition for the condition. In other embodiments, the composition is administered to a subject who has reached a particular age, or to a subject more likely to get the condition. In yet other embodiments, the compositions is administered to subjects who exhibit symptoms of the condition (e.g., early or advanced). In still other embodiments, the composition may be administered to a subject as a preventive measure. In some embodiments, the composition may be administered to a subject based on demographics or epidemiological studies, or to a subject in a particular field or career.

Administration of a composition of the invention may be accomplished by any medically acceptable method which allows the composition to reach its target. The particular mode selected will depend of course, upon factors such as those previously described, for example, the particular composition, the severity of the state of the subject being treated, the dosage required for therapeutic efficacy, etc. As used herein, a "medically acceptable" mode of treatment is a mode able to produce effective levels of the composition within the subject without causing clinically unacceptable adverse effects.

Any medically acceptable method may be used to administer the composition to the subject. The administration may be localized (i.e., to a particular region, physiological system, tissue, organ, or cell type) or systemic, depending on the condition to be treated. For example, the composition may be administered orally, vaginally, rectally, buccally, pulmonary, topically, nasally, transdermally, through parenteral injection or implantation, via surgical administration, or any other method of administration where access to the target by the composition of the invention is achieved. Examples of parenteral modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be preferred in some embodiments because of the convenience to the subject as well as the dosing schedule. Compositions suitable for oral administration may be presented as discrete units such as hard or soft capsules, pills, cachettes, tablets, troches, or lozenges, each containing a predetermined amount of the active compound. Other oral compositions suitable for use with the invention include solutions or suspensions in aqueous or non-aqueous liquids such as a syrup, an elixir, or an emulsion. In another set of embodiments, the composition may be used to fortify a food or a beverage.

In one set of embodiments, the compositions of the invention are administered by inhalation. For administration by inhalation, the compositions for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the compositions of the present invention, comprising the glutaredoxin. The compositions may be delivered to the lungs of a mammal while inhaling and traverses across the lung epithelial lining to the blood stream. Other reports of inhaled molecules include Adjei et al., 1990, *Pharmaceutical Research*, 7:565-569; Adjei et al., 1990, *International Journal of Pharmaceutics*, 63:135-144 (leuprolide acetate); Braquet et al., 1989, *Journal of Cardiovascular Pharmacology*, 13 (suppl. 5):143-146 (endothelin-1); Hubbard et al., 1989, *Annals of Internal Medicine*, Vol. III, pp. 206-212 (a1-antitrypsin); Smith et al., 1989, J. Clin. Invest. 84:1145-1146 (a-1-proteinase); Oswein et al., 1990, "Aerosolization of Proteins," *Proceedings of Symposium on Respiratory Drug Delivery II*, Keystone, Colo., March, (recombinant human growth hormone); Debs et al., 1988, *J. Immunol.*, 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the compositions of the present invention, for example, a glutaredoxin. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified glutaredoxins may also be prepared in different formulations depending on the type of chemical modification or the type of device employed.

Formulations suitable for use with a nebulizer, either jet or ultrasonic, will typically comprise a glutaredoxin or other composition as described herein, dissolved in water at a concentration of about 0.1 to 25 mg of biologically active glutaredoxin per mL of solution. The formulation may also include a buffer and a simple sugar (e.g., for stabilization of the glutaredoxin and regulation of osmotic pressure). The nebulizer formulation may also contain a surfactant to reduce or prevent surface induced aggregation of the glutaredoxin caused by atomization of the solution in forming the aerosol.

Formulations for use with a metered-dose inhaler device will generally comprise a finely divided powder containing the glutaredoxin, or other composition as described herein, suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the glutaredoxin (or other composition as described herein) and may also include a bulking agent, such as lactose, sorbitol, sucrose, or mannitol in amounts which facilitate dispersal of the powder from the device, e.g., 50 to 90% by weight of the formulation. The glutaredoxin may be prepared in particulate form with an average particle size of less than 10 mm (or microns), most preferably 0.5 to 5 mm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

For oral administration, the compounds can be formulated readily by combining the active composition(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally, the oral formulations may also be formulated in saline or buffers, i.e., EDTA for neutralizing internal acid conditions or may be administered without any carriers.

Also specifically contemplated are oral dosage forms of the above compositions. The compositions may be chemically modified, in some embodiments, so that oral delivery of the derivative is efficacious. Generally, the chemical modification contemplated is the attachment of at least one moiety to the composition itself, where said moiety permits (a) inhibition of proteolysis; and/or (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. See, e.g., Abuchowski and Davis, 1981, "Soluble Polymer-Enzyme Adducts," in: *Enzymes as Drugs*, Hocenberg and Roberts, Eds., Wiley-Interscience, New York, N.Y., pp. 367-383; Newmark, et al., 1982, *J. Appl. Biochem.* 4:185-189. Other polymers that could be used are poly-1,3-dioxolane and poly-1,3,6-tioxocane. Preferred for pharmaceutical usage are polyethylene glycol moieties.

For the compositions of the invention (or derivative), the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compositions of the present invention, or by release of the biologically active material beyond the stomach environment, such as in the intestine.

To ensure full gastric resistance a coating impermeable to at least pH 5.0 is usually required. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compositions of the present invention may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include, but are not limited to, starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into an aqueous environment, a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compositions of the present invention, either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compositions may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

The compositions, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compositions may be in powder form for constitution with a suitable vehicle, e.g., sterile pyrogen-free water, before use.

The compositions may also be formulated in rectal or vaginal compositions such as suppositories or retention enemas, e.g., containing conventional suppository bases such as cocoa butter or other glycerides.

In addition to the formulations described previously, the compositions may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

In certain embodiments of the invention, the administration of the composition of the invention may be designed so as to result in sequential exposures to the composition over a certain time period, for example, hours, days, weeks, months or years. This may be accomplished, for example, by repeated administrations of a composition of the invention by one of the methods described above, or by a sustained or controlled release delivery system in which the composition is delivered over a prolonged period without repeated administrations. Administration of the composition using such a delivery system may be, for example, by oral dosage forms, bolus injections, transdermal patches or subcutaneous implants. Maintaining a substantially constant concentration of the composition may be preferred in some cases.

Other delivery systems suitable for use with the present invention include time-release, delayed release, sustained release, or controlled release delivery systems. Such systems may avoid repeated administrations of the composition in many cases, increasing convenience to the subject. Many types of release delivery systems are available and known to those of ordinary skill in the art. They include, for example, polymer-based systems such as polylactic and/or polyglycolic acids, polyanhydrides, polycaprolactones and/or combinations of these; nonpolymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include, but are not limited to, erosional systems in which the composition is contained in a form within a matrix (for example, as described in U.S. Pat. Nos. 4,452,775, 4,675,189, and 5,736,152), or diffusional systems in which an active component controls the release rate (for example, as described in U.S. Pat. Nos. 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the composition. In addition, a pump-based hardware delivery system may be used to deliver one or more embodiments of the invention.

Use of a long-term release implant may be particularly suitable in some embodiments of the invention. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

Administration of the composition can be alone, or in combination with other therapeutic agents and/or compositions. In certain embodiments of the invention, a composition can be combined with a suitable pharmaceutically acceptable carrier, for example, as incorporated into a liposome, incorporated into a polymer release system, or suspended in a liquid, e.g., in a dissolved form or a colloidal form. In general, pharmaceutically acceptable carriers suitable for use in the invention are well-known to those of ordinary skill in the art. As used herein, a "pharmaceutically acceptable carrier" refers to a non-toxic material that does not significantly interfere with the effectiveness of the biological activity of the active compound(s) to be administered, but is used as a formulation ingredient, for example, to stabilize or protect the active compound(s) within the composition before use. The carrier may include one or more compatible solid or liquid fillers, diluents or encapsulating substances which are suitable for administration to a human or other vertebrate animal. The term "carrier" denotes an organic or inorganic ingredient, which may be natural or synthetic, with which one or more active compounds of the invention are combined to facilitate the application of the composition. The carrier may be co-mingled or otherwise mixed with one or more active compounds of the present invention, and with each other, in a manner such that there is no interaction which would substantially impair the desired pharmaceutical efficacy. The carrier may be either soluble or insoluble, depending on the application. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble. Those skilled in the art will know of other suitable carriers, or will be able to ascertain such, using only routine experimentation.

The formulations of the invention are administered in pharmaceutically acceptable solutions, which may routinely contain pharmaceutically acceptable concentrations of salt, buffering agents, preservatives, compatible carriers, adjuvants, emulsifiers, diluents, excipients, chelating agents, fillers, drying agents, antioxidants, antimicrobials, preservatives, binding agents, bulking agents, silicas, solubilizers, stabilizers and optionally other therapeutic ingredients, that may be used with the active compound. For example, if the formulation is a liquid, the carrier may be a solvent, partial solvent, or non-solvent, and may be aqueous or organically based. Examples of suitable formulation ingredients include diluents such as calcium carbonate, sodium carbonate, lactose, kaolin, calcium phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric acid and salts thereof, or phosphoric acid and salts thereof; or preservatives such as benzalkonium chloride, chlorobutanol, parabens, or thimerosal. Suitable carrier concentrations can be determined by those of ordinary skill in the art, using no more than routine experimentation. The compositions of the invention may be formulated into preparations in solid, semi-solid, liquid or gaseous forms such as tablets, capsules, elixirs, powders, granules, ointments, solutions, depositories, inhalants or injectables. Those of ordinary skill in the art will know of other suitable formulation ingredients, or will be able to ascertain such, using only routine experimentation.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Preparations include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. Those of skill in the art can readily determine the various parameters for preparing and formulating the compositions of the invention without resort to undue experimentation.

In some embodiments, the present invention includes the step of bringing a composition of the invention into association or contact with a suitable carrier, which may constitute one or more accessory ingredients. The final compositions may be prepared by any suitable technique, for example, by uniformly and intimately bringing the composition into association with a liquid carrier, a finely divided solid carrier or both, optionally with one or more formulation ingredients as previously described, and then, if necessary, shaping the product.

The compositions of the present invention, and optionally other therapeutics, may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. The term "pharmaceutically acceptable salts" includes salts of the composition, prepared in combination with, for example, acids or bases, depending on the particular compounds found within the composition and the treatment modality desired. Pharmaceutically acceptable salts can be prepared as alkaline metal salts, such as lithium, sodium, or potassium salts; or as alkaline earth salts, such as beryllium, magnesium or calcium salts. Examples of suitable bases that may be used to form salts include ammonium, or mineral bases such as sodium hydroxide, lithium hydroxide, potassium hydroxide, calcium hydroxide, magnesium hydroxide, and the like. Examples of suitable acids that may be used to form salts include inorganic or mineral acids such as hydrochloric, hydrobromic, hydroiodic, hydrofluoric, nitric, carbonic, monohydrogencarbonic, phosphoric, monohydrogenphosphoric, dihydrogenphosphoric, sulfuric, monohydrogensulfuric, phosphorous acids and the like. Other suitable acids include organic acids, for example, acetic, propionic, isobutyric, maleic, malonic, benzoic, succinic, suberic, fumaric, mandelic, phthalic, benzenesulfonic, p-tolylsulfonic, citric, tartaric, methanesulfonic, glucuronic, galacturonic, salicylic, formic, naphthalene-2-sulfonic, and the like. Still other suitable acids include amino acids such as arginate, aspartate, glutamate, and the like. Also, such salts can be prepared as alkaline metal or alkaline earth salts, such as sodium, potassium or calcium salts of the carboxylic acid group.

The present invention also provides any of the above-mentioned compositions in kits, optionally including instructions for use of the composition for the treatment of a condition characterized by an oxidative stress condition, for example, airway inflammation or asthma. That is, the kit can include a description of use of the composition for participation in any biological or chemical mechanism disclosed herein associated with an oxidative stress condition. The kits can further include a description of activity of the condition in treating the pathology, as opposed to the symptoms of the condition. That is, the kit can include a description of use of the compositions as discussed herein. The kit also can include instructions for use of a combination of two or more compositions of the invention, or instruction for use of a combination of a composition of the invention and one or more other compounds indicated for treatment of the oxidative stress condition. Instructions also may be provided for administering the composition by any suitable technique as previously described, for example, orally, intravenously, pump or implantable delivery device, or via another known route of drug delivery.

The kits described herein may also contain one or more containers, which may contain the composition and other ingredients as previously described. The kits also may contain instructions for mixing, diluting, and/or administrating the compositions of the invention in some cases. The kits also can include other containers with one or more solvents, surfactants, preservative and/or diluents (e.g., normal saline (0.9% NaCl), or 5% dextrose) as well as containers for mixing, diluting or administering the components in a sample or to a subject in need of such treatment.

The compositions of the kit may be provided as any suitable form, for example, as liquid solutions or as dried powders. When the composition provided is a dry powder, the composition may be reconstituted by the addition of a suitable solvent, which may also be provided. In embodiments where liquid forms of the composition are used, the liquid form may be concentrated or ready to use. The solvent will depend on the composition and the mode of use or administration. Suitable solvents for drug compositions are well known, for example as previously described, and are available in the literature. The solvent will depend on the composition and the mode of use or administration.

In still another aspect, the invention includes the promotion of one or more of the above-described embodiments, for example, promotion of methods for determining glutathionylated proteins and other oxidized proteins, e.g., in vitro or in vivo, promotion of treatment or prevention of an oxidative stress condition, e.g., by administering, to a subject, a composition comprising a glutaredoxin, such as GRX1 (GLRX) or GRX2 (GLRX2). As used herein, "promoted" includes all methods of doing business, including methods of education, scientific inquiry, academic research, industry activity including pharmaceutical industry activity, and any advertising or other promotional activity including written, oral and electronic communication of any form, associated with the invention.

Figure 12:
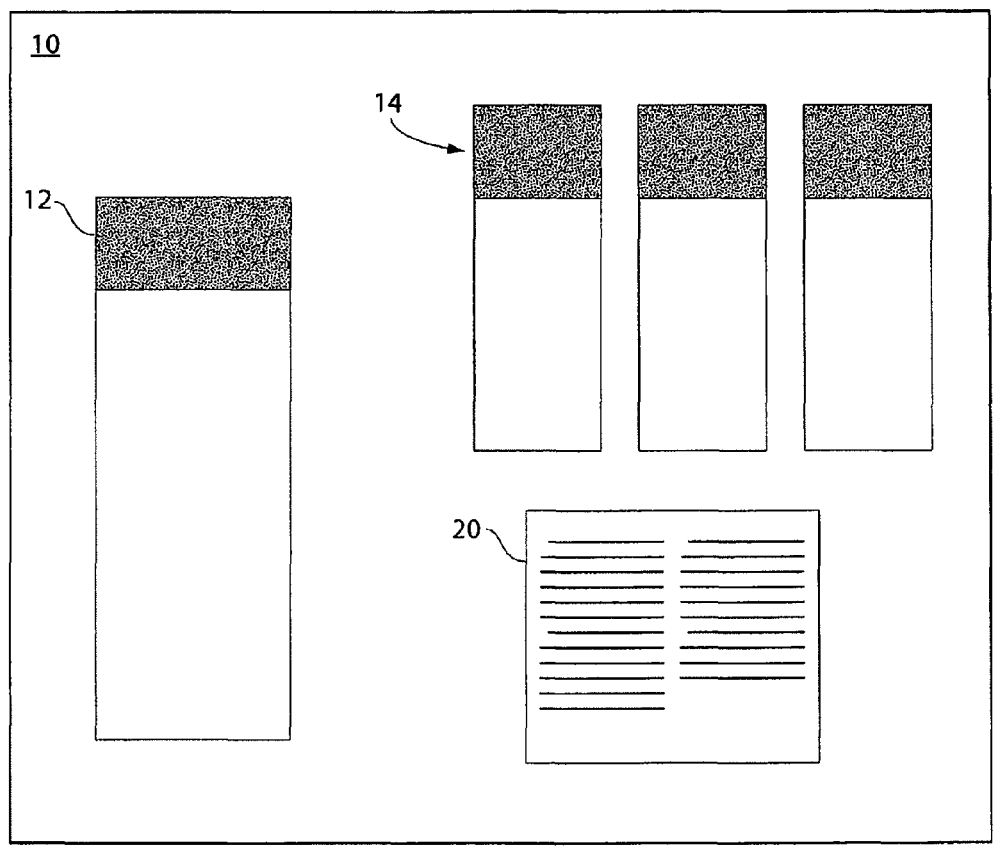
FIG. 12 depicts a kit with glutaredoxin therapeutics according to an embodiment of the invention (10=kit, 12=container of glutaredoxin, 14=container of additional components, 20=instructions).

An example of a kit useful according to the invention is shown in FIG. 12. The kit (1) shown in FIG. 12 includes a set of containers for housing glutaredoxin (12) and other compounds (14) as well as instructions (20).

The following applications are incorporated herein by reference: U.S. Provisional Patent Application Ser. No. 60/761,956, filed Jan. 25, 2006, entitled "Detection of Glutathionylated Proteins," by Y. Janssen-Heininger; and U.S. Provisional Patent Application Ser. No. 60/774,060, filed Feb. 16, 2006, entitled "Detection of Glutathionylated Proteins," by Y. Janssen-Heininger and U.S. patent application Ser. No. 11/698,300 filed on Jan. 25, 2007, entitled "Detection of Glutathionylated Proteins," by Y. Janssen-Heininger.

The following examples are intended to illustrate certain aspects of certain embodiments of the present invention, but do not exemplify the full scope of the invention.

Example 1

Figure 1B:
Figure 1C:

This example illustrates that visualization of protein S-glutathionylation (PSSG) using the GRX-catalyzed cysteine derivatization in lung tissues of mice demonstrated increases in reactivity in mice with allergic airways disease (FIG. 1). The mice were injected intraperitoneally with 40 micrograms of ovalbumin with the adjuvant aluminum hydroxide ("Alum") (Pierce Chemical, Rockford, Ill.) on days 1 and 7 to induce sensitivzation. Sham sensitized mice received Alum alone. The mice were then exposed to an aerosolized 1% ovalbumin solution in sterile phosphate-buffered saline (PBS) for 30 minutes on days 14 through 19. Lung tissue was then harvested 2 days (day 21) following the final ovalbumin challenge. FIG. 1C shows ovalbumin (Ova) sensitization and challenge (Ova/Ova). Alum/Ova denotes control group (FIG. 1B). FIG. 1C shows increases in PSSG reactivity on the apical surface of airway epithelial cells. A control assay (FIG. 1A) was performed on lung tissue in the absence of GRX. Increases in reactivity were observed on the apical surfaces of airway epithelial cells, which suggested that PSSG stress occurred on the external surfaces, providing evidence that GRX can be administered therapeutically.

Recombinant GRX1 was administered to cell culture medium containing A549 lung epithelial cells, and 24 hours later PSSG was visualized using GRX-catalyzed cysteine derivatization. In the controls, no GRX1 was administered. While baseline S-glutathionylation was observed in the control cells (FIGS. 2A and 2B) cultures where GRX was added exogenously demonstrated decreases in the intracellular content of PSSG (FIGS. 2C and 2D).

Figure 3:
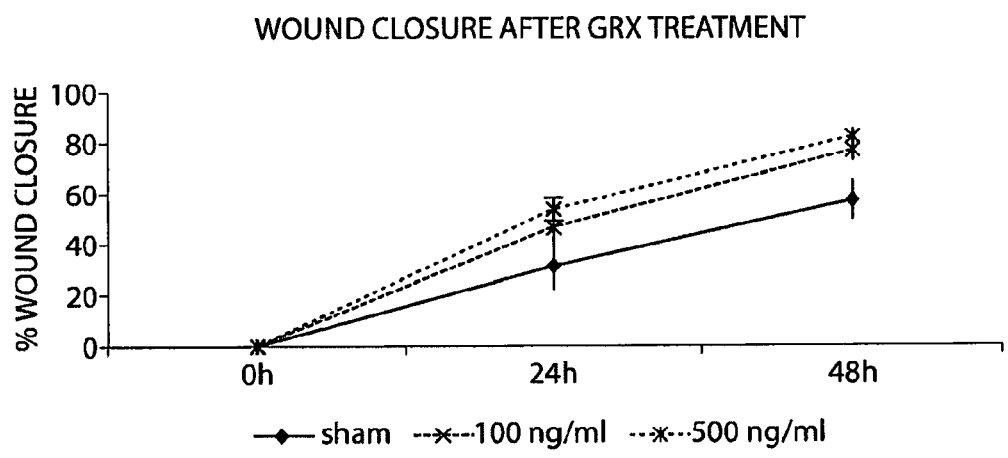
FIG. 3 is a graph illustrating that administration of GRX improved wound healing, according to yet another embodiment of the invention.

The functional significance of reduced S-glutathionylation was demonstrated in wound healing experiments. An artificial, linear wound was created in confluent monolayers of A549 using a 200 microliter pipet tip, and the dislodged cells were washed out using media. Fresh media was added with 100 or 500 ng/ml GRX1. Initial wound sizes were measured from photographs using NIH ImageJ software. 24 or 48 hours later wound closure was measured again to measure wound size, and wound closure was expressed as a percentage of the initial wound area. FIG. 3 demonstrates that exogenous administration of GRX1 improved wound healing.

Collectively, these results demonstrate that administration of GRX1 can be used therapeutically to improve wound healing. This has relevance for diseases such as Acute Respiratory Distress Syndrome, where epithelial barrier function is compromised, leading to edema or respiratory distress. Similarly, other diseases which are accompanied by oxidative imbalances could benefit from administration of GRX to correct the status of protein-S-glutathionylation.

Example 2

In this example, the expression of GRX in a mouse model of allergic airway disease was investigated. Furthermore, the modulation of GRX by cytokines that were relevant to allergic airway disease was examined in primary mouse tracheal epithelial cells.

The following are certain protocols and methods used in this example.

Six to 8 week-old female C57BL/6 mice (Jackson Laboratories) were housed in the University of Vermont Animal Facility. Mice were subjected to ovalbumin (OVA) sensitization and challenge as described in Poynter, M. E., et al., "Rapid Activation of Nuclear Factor Kappa B in Airway Epithelium in a Murine Model of Allergic Airway Inflammation." *Am. J Pathol.*, 2002, 160 (4):1325-1334, incorporated herein by reference.

Primary epithelial cells were isolated from the C57BL/6 mice according to published techniques (see Reynaert, N. L., et al., "In situ Detection of S-Glutathionylated Proteins following Glutaredoxin-1 Catalyzed Cysteine Derivatization," *Biochim Biophys Acta* 2006; 1760 (3):180-187), incorporated by reference herein. The cells were plated on Collagen I coated culture dishes or glass slides, and switched to phenol red free DMEM/F12 media containing 2 mM L-glutamine and P/S 24 h before initiation of experiments.

Total RNA was isolated from lung using an RNeasy Mini Kit (Qiagen, Valencia, Calif.), DNase treated, and reverse transcribed into cDNA. Semiquantitative TaqMan PCR for GRX1 and 2 were performed (Applied Biosystems, Framingham, Mass.) and values were normalized to HPRT. The primers were obtained from Applied Biosystems.

Following euthanasia, the lungs were instilled with 50% Tissue-Tek OCT Compound (Sakura Finetek Inc., Torrance, Calif.) in PBS and frozen in liquid nitrogen-chilled isopentane for the preparation of 10-micrometer frozen sections. The slides or cells were fixed with 4% paraformaldehyde (PFA), washed, and permeabilized with 1% Triton X-100 in PBS for 20 min. After blocking with 1% BSA in PBS (PBS/ 1% BSA), the slides were incubated with rabbit anti-human GRX1 antibody (10 micrograms/ml, Labfrontier) overnight at 4° C. Following three washes in PBS/1% BSA, the slides were incubated with goat anti-rabbit Cy3 secondary antibody (Jackson ImmunoResearch Laboratories, West Grove, Pa.) and counterstained with Sytox Green (Molecular Probes) to label the DNA. The slides were washed and coverslipped, and sections were scanned using an Olympus BX50 upright microscope configured to a Bio-Rad MRC 1024 confocal scanning laser microscope system using a 20× objective.

The lung lysates were mixed with 2× Laemmli sample buffer, boiled, and loaded on polyacrylamide gels. The proteins were transferred to nitrocellulose and Western blotting for GRX1 was performed using a GRX1 antibody (Labfrontier) as previously described (Reynaert, N. L., et al., "In situ Detection of S-Glutathionylated Proteins following Glutaredoxin-1 Catalyzed Cysteine Derivatization," *Biochim Biophys Acta* 2006; 1760 (3):180-187).

GRX activity was assayed as follows. Briefly, cells or lungs were lysed in buffer containing 137 mM Tris-HCl (pH 8.0), 130 mM NaCl, 1% NP-40, and cleared by centrifugation and equalized for protein content. For analysis of whole lung GRX activity, excess NADPH was removed from lung lysates through a Micro Bio-Spin 6 chromatography column (Bio-Rad) prior to analysis. The lysates were incubated with reaction buffer containing 137 mM Tris-HCl (pH 8.0), 0.5 mM GSH, 1.2 units GSSG reductase (Roche), 0.35 mM NADPH, 1.5 mM EDTA (pH 8.0) and 2.5 mM Cys-$SO_3$. The reaction was allowed to proceed at 30° C., and the NAPDH consumption was followed spectrophotometrically at 340 nm. The data are expressed as units, where 1 unit equals the oxidation of 1 micromolar NADPH/min/mg protein.

The assessment of GRX1-catalyzed cysteine derivatization to visualize S-glutathionylation was performed as follows. Cells were grown on Collagen I coated glass slides and exposed to test agents, and S-glutathionylation was assessed using GRX1-catalyzed cysteine derivatization, using techniques similar to those described above. This assay is based on a biotin switch, and utilizes a procedure which encompasses cell permeabilization and chemical blocking of reduced thiol groups using a buffer containing 25 mM Hepes, pH 7.7, 0.1 mM EDTA, 0.01 mM neocuproine, 20 mM N-ethylmaleimide and 1% Triton X-100 for 30 min at 4° C., followed by GRX1-dependent reduction of protein-glutathione mixed disulfides using 27 microgram/ml *E. coli* or human GRX1 (American Diagnostica), 4 U/ml GSSG reductase (Roche), 1 mM GSH, 1 mM NADPH and 1 mM EDTA in 50 mM Tris, pH 7.5, for 15 mM at 37° C. The newly reduced sulfhydryl groups were labeled with 1 mM N-(3-maleimidylpropionyl) biocytin (MPB, Molecular Probes) for 1 h at RT and visualized using streptavidin-Alexa Fluor 568. The nuclei were counterstained with Sytox Green and the slides were analyzed by confocal microscopy using a 20× objective.

Figure 4A:
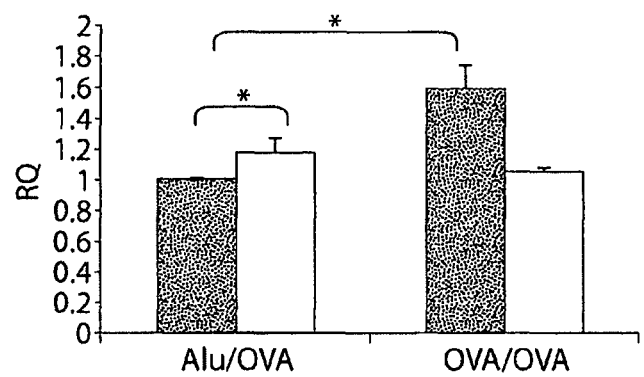
FIGS. 4A-4F illustrate data showing that GRX expression is increased in allergic airway disease.

The in vivo data were expressed as mean±SEM, and were compared by analysis of variance (ANOVA). Differences were considered significant when $p<0.05$. All experiments were repeated at least two times. In FIG. 4, RNA was collected from lungs 48 h after the last challenge, reverse-transcribed and analyzed for GRX1 (filled) and 2 (open) expression relative to HPRT by TaqMan PCR. Data are expressed as mean RQ from five mice per group (±SEM). * represents $p<0.05$ GRX was found to be increased in allergic airway disease. The immunization and challenge with Ova caused eosinophilic inflammation and marked increases in levels of, amongst others, Interleukins 4, 5, 6; KC (a chemokine); and MCP1 (monocyte chemoattractant protein-1) in BALF (bronchoalveolar lavage fluid). The total lung homogenates from mock-sensitized (Alu/OVA) mice expressed both GRX1 and GRX2 mRNA. The basal expression of GRX2 mRNA in lung tissue was significantly higher then that of GRX1. The antigen sensitization and challenge (OVA/OVA) increased mRNA levels of GRX1 (filled), while not affecting GRX2 (open) mRNA levels (FIG. 4A).

Figure 4B:
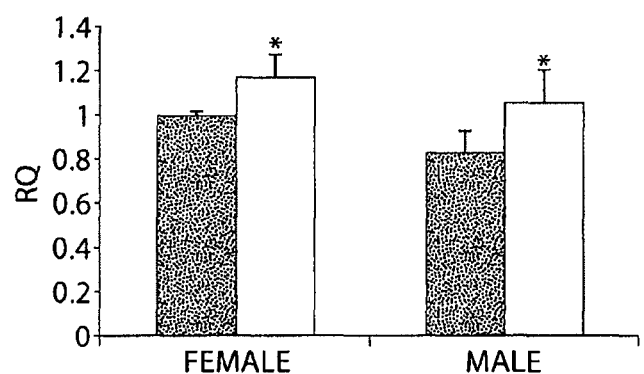

In FIG. 4B, RNA was collected from lungs of mock-sensitized male and female mice 48 h after the last challenge and analyzed for GRX1 (filled) and 2 (open) expression relative to HPRT by TaqMan PCR. Data are expressed as mean RQ from five mice per group (±SEM). * represents p<0.05 between GRX1 and GRX2. Since GRX1 mRNA expression was believed to be higher in the brain of female compared to male mice, and this was associated with protection against the induction of experimental Parkinson's disease, the differential expression of GRX in lungs of both sexes was investigated. FIG. 4B demonstrated that in contrast to the brain, lungs of control male or female mice displayed no significant differences in the levels of either GRX1 or GRX2 mRNA, nor differences in GRX activity (data not shown).

Figure 4C:
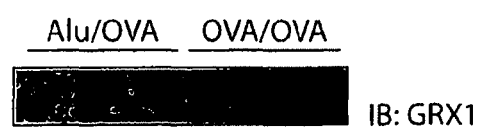
Figure 4D:
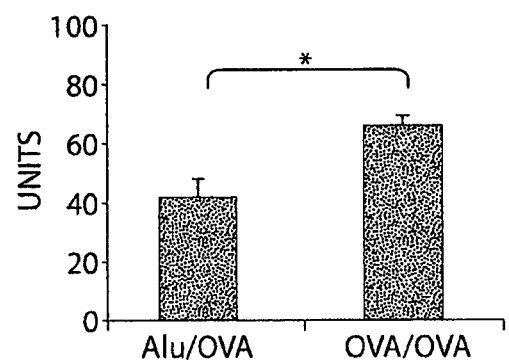
Figure 4E:
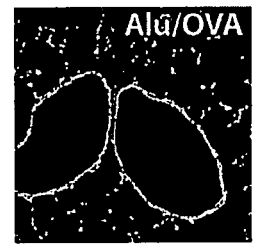
Figure 4F:
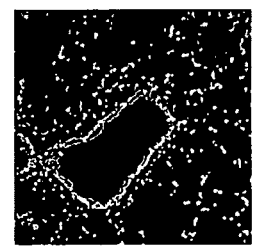

To corroborate increases in GRX1 mRNA expression in response to OVA, Western blot analysis was performed on lung lysates for GRX1. These results are shown in FIG. 4C, demonstrating elevated levels of GRX1 protein in whole lung homogenates after sensitization and challenge with OVA when compared to mock-sensitized controls, which corresponded to increases in GRX activity (FIG. 4D). The GRX activity was assessed in lung lysates as described above. The result shown here is representative of three experiments and values are mean from three mice per group (±SEM). Immunofluoresence analysis of lung sections revealed that in naive mice, GRX1 was localized to both airways and parenchyma, and increased predominantly in the airway epithelium in this experimental model of allergic airway disease (FIG. 4E). The frozen sections were stained with an antibody directed against GRX1, followed by incubation with a Cy3 conjugated secondary antibody. Sytox Green was used as a nuclear counter stain and sections were scanned by confocal microscopy. The images are representative of results from five to six mice per group. Collectively, these data indicate that lung GRX1 expression increased in allergic airway disease and that this corresponded to elevated levels of GRX activity.

Additionally, experiments were performed to determine regulation of GRX1 and S-glutathionylation by IFNγ (IFN gamma) and TGFβ (TGF beta) in vitro. Since little information exists on the regulation of GRX expression and activity, primary mouse tracheal epithelial cells were exposed to cytokines relevant to asthma. The experiments were generally focused on tracheal epithelial cells since these cells demonstrated high levels of GRX expression (FIGS. 4E and 4F) and were believed to play an important role in the defense against oxidants and the regulation of innate and adaptive immune responses. While no significant effects were observed in response to TNFα (TNF alpha) on GRX activity, LPS (lipopolysaccharide), CpG DNA, IL-4, or TGFβ1 (TGF beta-1) decreased GRX enzymatic activity (Table 1). In contrast, IL-13 and IFNγ (IFN gamma) were the only mediators tested that caused an increase in GRX activity (Table 1). Cells were treated for 48 h with each agent at the following concentrations: 20 ng/ml TNFα, 5 µg/ml LPS, 1 µg/ml CpG DNA, 10 pg/ml IL-13, 20 ng/ml IL-4, 20 pg/ml IFNγ or 10 ng/ml TGFβ, and GRX activity was determined.

TABLE 1

GRX activity in primary airway epithelial cells.

| | Fold change | p-value |
|---|---|---|
| Sham | 1 | |
| TNFα | 0.76 ± 0.07 | 0.19 |
| LPS | 0.89 ± 0.07 | 0.03 |
| CpG DNA | 0.71 ± 0.003 | 0.03 |
| IL-13 | 1.42 ± 0.27 | 0.01 |
| IL-4 | 0.73 ± 0.07 | 0.03 |
| TGFβ | 0.60 ± 0.02 | 0.01 |
| IFNγ | 1.93 ± 0.05 | 0.002 |

Figure 5A:
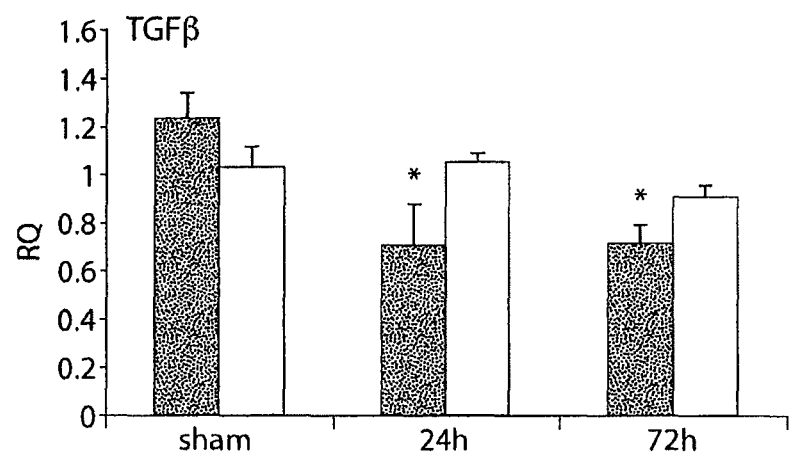
Figure 5B:
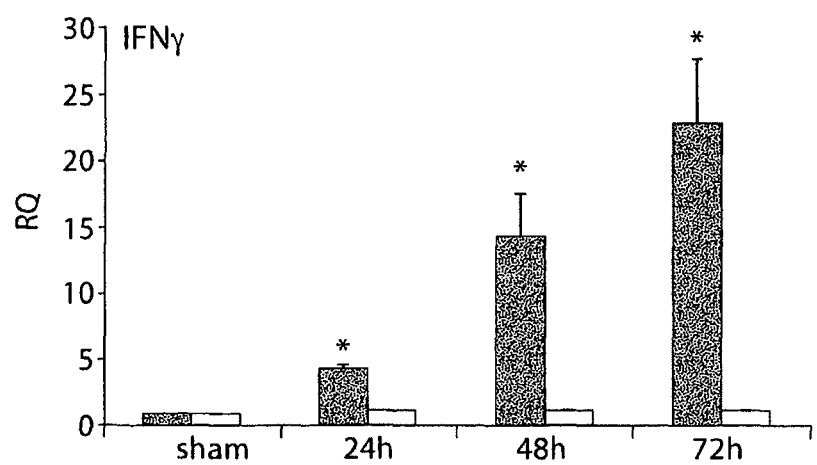

Since TGFβ1 (TGF beta-1) and IFNγ (IFN gamma) caused the strongest modulation of GRX activity, GRX expression profiles and protein S-glutathionylation were further evaluated in response to these cytokines. Consistent with decreases in GRX activity, TGFβ1 (TGF beta-1) caused attenuated expression of GRX1 mRNA (filled), while not affecting GRX2 mRNA (open) levels (FIG. 5A). FIG. 5A shows primary airway epithelial cells treated with 5 ng/ml TGFβ1 (TGF beta-1) and FIG. 5B shows 20 pg/ml IFNγ (IFN gamma). For the indicated time frames, mRNA was collected, reverse-transcribed and analyzed for GRX1 (filled) and 2 (open) expression relative to HPRT by TaqMan PCR. Data are expressed as mean (±SD) and * represents p<0.05. FIGS. 5C-5J show primary airway epithelial cells treated with 5 ng/ml TGFβ (TGF beta) or 20 pg/ml IFNγ (IFN gamma) for 48 h. FIGS. 5C-5F show immunohistochemistry for GRX1 and nuclei counterstained with Sytox Green. FIGS. 5G-5J show GRX1-reversible cysteine oxidation and nuclei counterstained with Sytox Green. As reagent controls, either primary antibody (FIGS. 5C-5F) or GRX (GRX, FIGS. 5G-5J) were omitted from the reaction mix.

Although clear decreases in GRX1 protein levels were not detected in response to TGFβ (TGF beta) compared to controls (FIG. 5C-5F) via immunofluorescence, possibly due to the low level of staining present in control cells, TGFβ (TGF beta) did result in marked increases in protein S-glutathionylation (FIG. 5G-5J). Consistent with the increases in GRX activity in cells exposed to IFNγ (IFN gamma) (Table 1), exposure to IFNγ (IFN gamma) resulted in increased expression of GRX1 mRNA, whereas GRX2 mRNA levels were not affected (FIG. 5B). Concomitant increases in GRX1 protein levels (FIG. 5C-5F), and decreases in protein S-glutathionylation (FIG. 5G-5J) were also detected by immunofluorescence in cells exposed to IFNγ (IFN gamma).

In this example, GRX1 was identified as part of the antioxidant defense system of the lungs that is upregulated during allergic airway disease. Although basal expression levels of GRX2 mRNA were higher than GRX1, only increases in GRX1 mRNA were detected in lung tissue of mice with allergic airway disease (FIG. 4). The two isoforms of GRX did not only differ in their intracellular localization, but they may be differentially regulated as well. GRX2 may be a redox sensor that is inactive as a dimer through the formation of a 2Fe-2S cluster. Upon oxidative stress, GRX2 may be activated through oxidation of the 2Fe-2S cluster and its subsequent monomerization. This example demonstrates that GRX1 mRNA levels increased after treatment with IFNγ (IFN gamma) while conversely, TGFβ (TGF beta) treatment led to repressed expression of GRX1 mRNA (FIGS. 5B and 5A, respectively). These findings also suggested that GRX1 is regulated at the transcriptional level, whereas GRX2 may be regulated posttranslationally. Such diverse regulatory mechanisms would allow for quick activation of GRX2 upon oxidative stress to confer rapid restoration of sulfhydryl groups, whereas GRX1 would provide delayed but sustained protection. In addition, this data shows that mRNA of GRX can also be used as a therapeutic under some conditions.

In the current example, IFNγ (IFN gamma) enhanced GRX1 mRNA levels in primary tracheal epithelial cells. The antioxidant enzymes thioredoxin reductase and MnSOD have also been demonstrated to be positively regulated by IFNγ (IFN gamma). The promoter region of the human GRX1 gene, however, does not contain GAS elements, and IFNγ (IFN gamma) may act in concert with other transcription factors to induce GRX1. Alternatively, given the late induction of GRX1 mRNA after IFNγ (IFN gamma) stimulation, it is possible that intermediate IFNγ (IFN gamma)-driven factors, such as interferon regulatory factors 1 and 2, may be involved in inducing GRX1 transcription in a type 2 IFN response. Repression of GRX1 expression by TGFβ (TGF beta) was also observed previously. Surprisingly, a repressive effect of TGFβ (TGF beta) has also been reported towards multiple other antioxidant enzymes, like for instance catalase, MnSOD, Cu, ZnSOD, gamma-glutamylcysteinyl synthetase. Although the mechanism and functional outcome of repression of antioxidant defenses by TGFβ (TGF beta) remain elusive, several potential interactions between TGFβ (TGF beta) and oxidants/antioxidants in the lung have been described, and it is thought that oxidants and TGFβ (TGF beta) may co-operate to enhance fibrotic responses. Altered levels of protein S-glutathionylation in response to TGFβ (TGF beta) or IFNγ (IFN gamma) could be the result of not only alterations in GRX1 expression and overall GRX activity, but could also arise from changes in total GSH and GSH/GSSG ratios. For instance, TGFβ (TGF beta) may decrease GSH synthesis, which can lower GSH/GSSG and drive S-glutathionylation by GRX.

Asthma or allergic airway disease is characterized by a Th-2 bias. GRX1 expression is elevated during allergic airway disease, but GRX1 appears to be negatively regulated by at least two Th-2 associated cytokines, TGFβ (TGF beta) and IL-4, whereas the Th-1 cytokine IFNγ (IFN gamma) positively impacted on GRX1 expression. While at first glance these results seem contradictory, Th-1 co-development has been demonstrated to occur during allergic airway inflammation and IFNγ (IFN gamma) in particular has been found to be elevated in mouse models that use similar protocols to the one used in this current study. An increase in GRX1 and total GRX activity during allergic airway disease could be part of the protective antioxidant defense of the lung. Through its deglutathiolating activity, GRX1 could be responsible for liberating GSH from proteins in order to increase GSH levels to combat the oxidant stress associated with the inflammatory response.

Additionally, alterations in the kinetics and extent of protein S-glutathionylation that occur in association with alterations in GRX1 expression and activity could play an important role in the disease process by affecting cell signaling cascades. For instance, S-glutathionylation of the p50 and c-Jun subunit of the transcription factors NF-κB (NF kappa B) and AP-1 may prevent DNA-binding and consequent inflammatory gene transcription. Alternatively, enhanced S-glutathionylation of protein tyrosine phosphatase 1B following NADPH oxidase activation in macrophages may be important to the activation of tyrosine kinases.

In vivo GRX1 expression appears to be mainly localized to airway epithelium (FIG. 4E). Airway epithelium represents an important barrier of the lungs and may confer antioxidant protection. Thus, GRX1 expression may be prominently localized in epithelia under basal conditions, in addition to being upregulated during allergic airway inflammation (FIG. 4E).

In summary, the present example provides the first evidence that expression of GRX is altered in mice with allergic airway inflammation. Given the emerging significance of GRX catalytic activity both in antioxidant defenses and cell signaling, this enzyme could play a critical role in the etiology of allergic airway inflammation.

Example 3

Figure 6A:
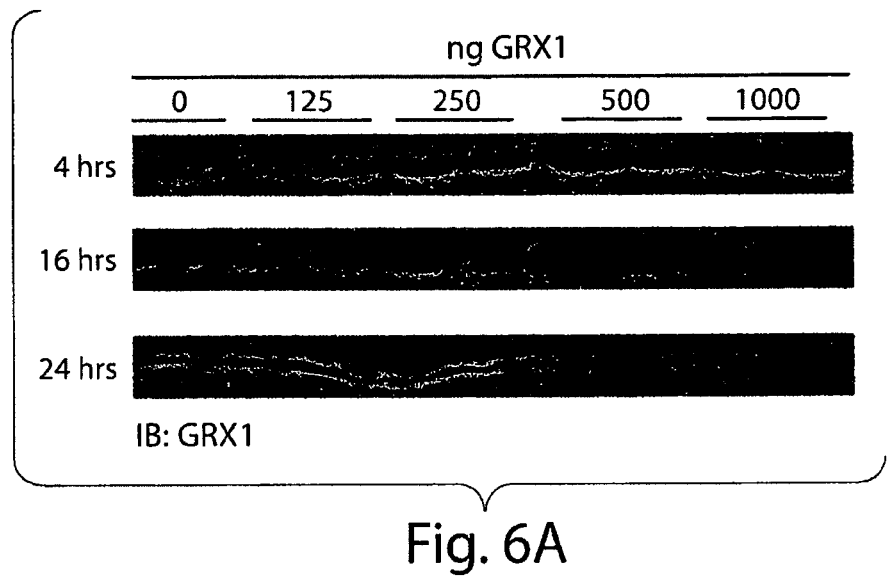
FIGS. 6A-B illustrate data showing clearance of recombinant GRX1 from cells according to one embodiment of the invention.
Figure 6B:
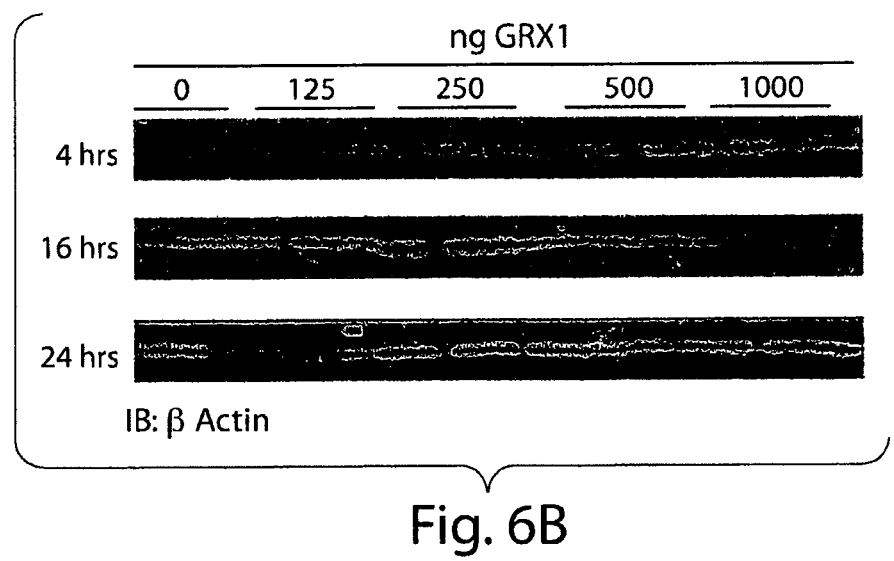

Direct evidence to support the uptake of recombinant GRX1 into cells was obtained following incubation of lung epithelial cells. Confluent C10 cells were grown in medium supplemented with 5% fetal bovine serum, 1 mM L-glutamine, and 0.5% streptomycin/penicillin. Prior to treatment cells were starved for 2 hours in medium supplemented with 0.5% FBS. Cells were then loaded with recombinant glutaredoxin 1 (GRX1) at concentrations ranging form 125-1000 ng (FIG. 6) and incubated for 4, 16, and 24 hours. Cells were then washed extensively with ice cold PBS and lysed in buffer containing 50 mM Tris HCl pH 8.0, 135 mM NaCl, 1% NP-40, supplemented with protease inhibitors. Lysates were cleared by centrifugation and 45 µg of protein loaded onto a 15% polyacrylamide gel for western blot analysis using an anti-GRX1 antibody (FIG. 6A), or and anti-β actin antibody (FIG. 6B). Note that the actin blot was provided as a reagent control to ascertain that equal amounts of protein were loaded in each lane. At selected times post-administration of GRX1 to cell culture medium, cells were lysed, lysates were centrifuged, and supernatants were used for Western Blotting. Results in FIG. 6 demonstrate that administration of recombinant GRX1 lead to a dose and time dependent increase in the content of GRX1 within the cell lysates, consistent with its uptake, and its ability to decrease PSSG shown in FIG. 2.

Figure 8A:
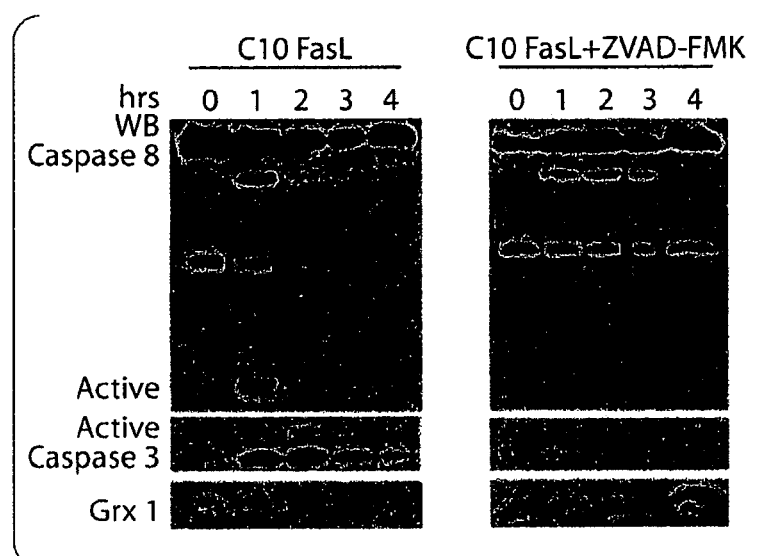
FIGS. 8A-B show the induction of apoptosis in lung epithelial cells though ligation of the Fas death receptor, according to one embodiment of the invention.
Figure 8B:
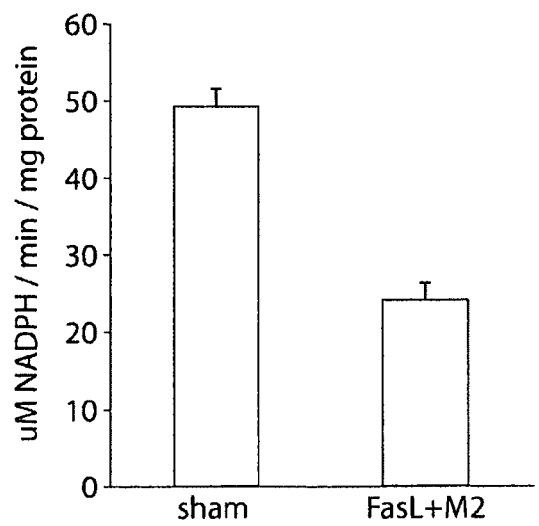

We have noted that at later timepoints (not shown) GRX1 disappears from cells, through a mechanism that is still unclear. Cells possess an extensive machinery of proteolytic enzymes, and protein degradation machinery to regulate the content of proteins, and it is possible that GRX1 expression may be regulated via proteolysis, which might limit its therapeutic potential. In order to investigate this we scanned the public data bases for putative sites of post-translational modification and potential protease cleavage sites. The result of this analysis are depicted in FIG. 7, which shows potential glycosylation sites and PKC phosphorylation sites. In addition, FIG. 7 shows the putative caspase cleavage site within mouse GRX1, a site that also is present in human GRX1. We therefore evaluated whether GRX1 can be a target for degradation by caspases. First we treated C10 mouse lung epithelial cells with a caspase inducing death receptor ligand, FasL (plus cross linking agent). FIG. 8A shows that induction of apoptosis in lung epithelial cells via ligation of the Fas death receptor, using Fas Ligand results in the formation of active caspase 8 and 3 (left) and degradation of GRX1 (FIG. 8A bottom left panel). In addition, inhibition of caspases with the generic caspase inhibitor, ZVADFMK, (FIG. 8A right panel) prevents the degradation of GRX1. FIG. 8B shows that induction of apoptosis in lung epithelial cells via ligation of the Fas death receptor, using Fas Ligand results in a 50% decrease in catalytic activity of GRX1 in lung epithelial cells. Thus, the results presented in FIG. 8 demonstrate that in cells exposed to FasL, caspase activation occurs, based upon the formation of cleaved versions of caspases 8 and 3 (the active variants). Importantly in the same experiment, GRX1 expression decreased in cells. However, in cells treated with a generic inhibitor of caspases, Z-VAD, GRX1 levels remained intact, suggesting that active caspases led to degradation of GRX1.

Figure 9:
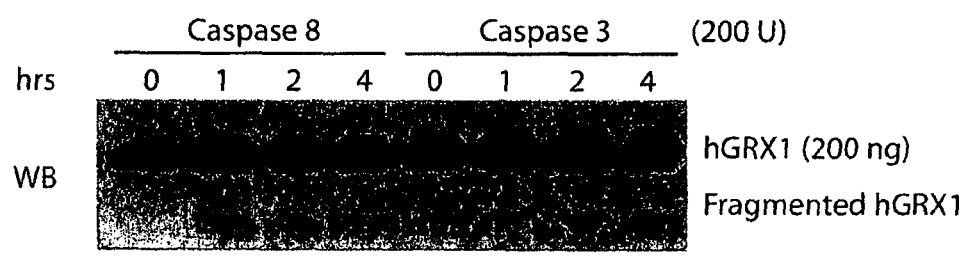
FIG. 9 shows the cleavage of human GRX1 by recombinant Caspase 3 or recombinant Caspase 8, according to one embodiment of the invention.

In the next experiment, we incubated recombinant GRX1 in a test tube with active Caspases 8 and 3. Treatment of recombinant human GRX1 with recombinant Caspase 8 or 3 results in cleavage of GRX1, as demonstrated via Western Blotting (WB), which also revealed the appearance of a smaller fragment of GRX1 (FIG. 9). Preliminary analysis shows that the size of the fragment is consistent with cleavage at the putative caspase site, (As shown in FIG. 7). The results presented in FIG. 9 demonstrate that Caspases 3 or 8 are directly capable of degrading GRX1.

Figure 10A:
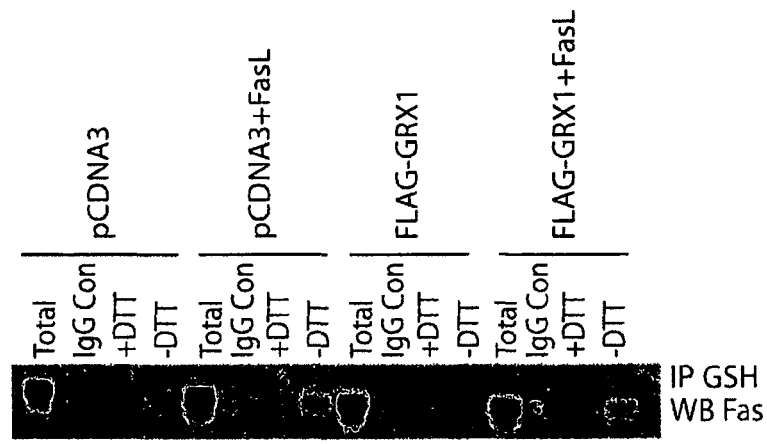
FIGS. 10A-B shows the relationship between GRX1 and Fas, according to one embodiment of the invention.
Figure 10B:
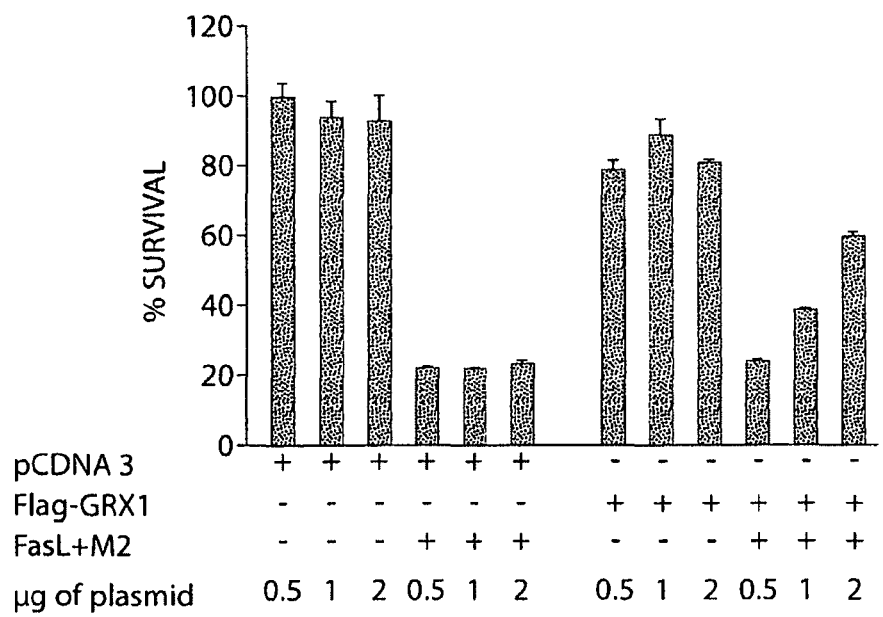

The functional importance of caspase dependent degradation was further elucidated in experiments where we overexpressed GRX1 or knocked down GRX1 expression via siRNA strategies. Cells were mock transfected (PcDNA3) or transfected with GRX1, and either left untreated, or exposed to the death inducing ligand, FasL. S-glutathionylated proteins were immunoprecipitated with an antibody recognizing GSH (IP GSH), subjected to non-reducing electrophoresis for detection of Fas by Western Blot (WB Fas) (See FIG. 10A). The −DTT lanes demonstrate S-glutathionylation of Fas, whereas the +DTT lanes are reagent controls. Note the marked reactivity of Fas glutathionylation in response to Fas ligation, which is markedly decreased in cells transfected with GRX1. FIG. 10B shows that GRX1 overexpression partially rescues cells from FasL induced cell death. Cell survival was assessed using the MTT assay. FIG. 10 therefore shows that Fas is a target for S-glutathionylation in response to ligation of its receptor FasL, which can be reversed by overexpression of GRX1.

Figure 11A:
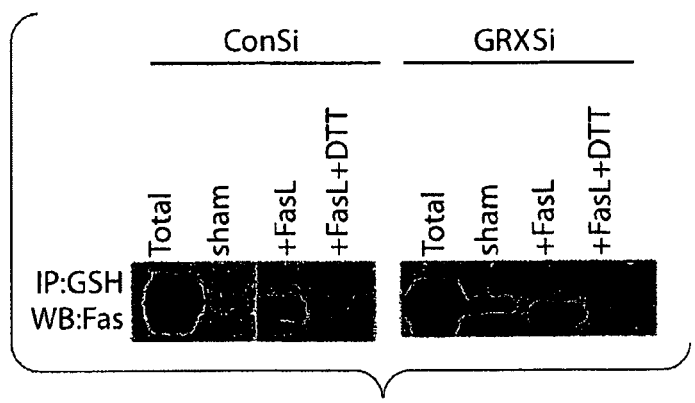
FIGS. 11A-C show that FasL-induced S-glutathionylation is increased following siRNA knock-down of GRX1, according to one embodiment of the invention.
Figure 11B:
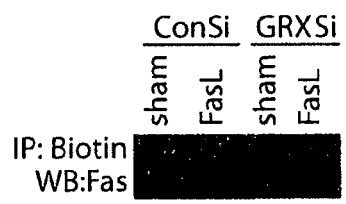
Figure 11C:
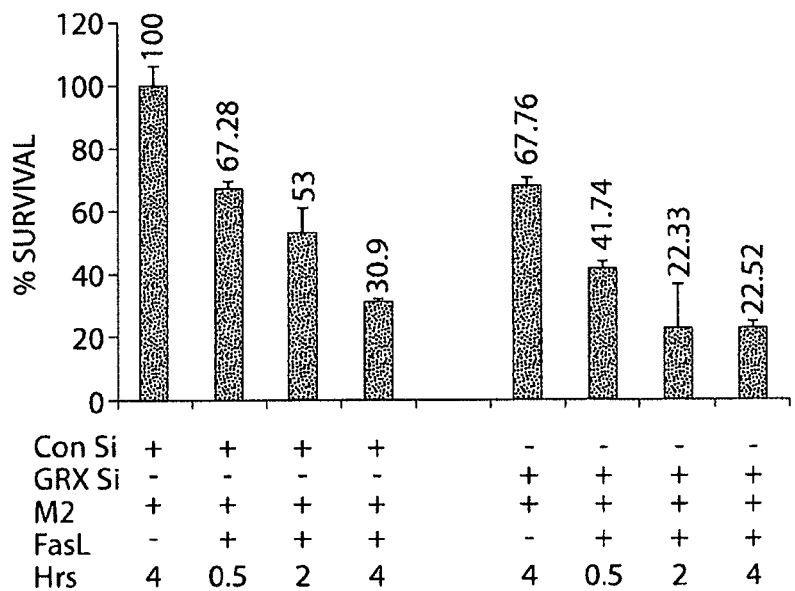

FIG. 11 shows that FasL-induced S-glutathionylation of Fas is increased following SiRNA knock-down of GRX1. Cells were mock transfected (ConSi) or transfected with GRX1 SiRNA (GRXSi), and either left untreated, or exposed to the death inducing ligand, FasL (See FIG. 11A). S-glutathionylated proteins were immunoprecipitated with an antibody recognizing GSH (IP GSH), subjected to non-reducing electrophoresis, for detection of Fas by Western Blot (WB Fas). The +DTT lanes are reagent controls, and the Total lane represents Fas in the whole cell lysate not subjected to immunoprecipitation. Note that Fas glutathionylation is enhanced in GrxSi RNA treated samples, even in absence of Fas Ligation (Sham). FIG. 11B shows enhanced Fas S-glutathionylation in control conditions, and following Fas ligation (FasL) in response to knock down of GRX1 (GrxSi). In this experiment, cells were loaded with biotinylated cell permeable GSH ester, and protein glutathionylation detected following immunoprecipitation of S-glutathionylated proteins with an antibody against biotin (IP Biotin), Fas S-glutathionylation was detected in a Western blot. FIG. 11C shows that siRNA knock down of GRX1 enhances cells to spontaneous cell death, and cell death in response to FasL plus crosslinking antibody, M2. Cell survival was assessed using the MTT assay. Con Si is control siRNA used as a reagent control.

The experiments presented in FIGS. 10 and 11 demonstrated that FasL induces death of epithelial cells. GRX1 overexpression attenuated cell death, whereas knock-down of GRX1 enhanced cell death. The data also show that GRX1 status regulates protein S-glutathionylation. Specifically, we have demonstrated that in response to FasL stimulation, Fas itself becomes S-glutathionylated. FasL-induced S-glutathionylation of the Fas receptor was enhanced in cells following knock down of GRX1, whereas S-glutathionylation of Fas was decreased in cells overexpressing GRX1, consistent with regulating cell death (FIGS. 10 and 11).

These research findings demonstrate that the expression levels of GRX1 directly regulate cell survival and death, in conjunction with its role in controlling protein S-glutathionylation. We also demonstrated that GRX1 is a target for degradation by the Caspase family of proteases, and predict that mutant forms of GRX1 that lack Caspase cleavage sites will be superior as a therapeutic compound. These research findings of Caspase induced degradation of GRX1 elucidates the mechanism of tissue homeostasis, and allows for therapeutic intervention in disease conditions such as cancer.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. A composition, comprising a glutaredoxin, wherein the glutaredoxin has an inactivated caspase cleavage site, wherein the inactivated caspase cleavage site comprises Glu-Phe-Val-Asp (SEQ ID NO:9).

2. The composition of claim 1, wherein the glutaredoxin is GRX1.

3. The composition of claim 1, wherein the glutaredoxin has an identity of greater than 90% with GRX1.

4. The composition of claim 1, wherein the glutaredoxin active site comprises Cys-Pro-Tyr-Cys (SEQ ID NO:1), Cys-Ser-Tyr-Cys (SEQ ID NO:2) or Cys-Gly-Phe-Ser (SEQ ID NO:3).

5. The composition of claim 1, wherein the glutaredoxin is a human glutaredoxin.

6. The composition of claim 1, wherein the glutaredoxin is not human lens thioltransferase.

7. The composition of claim 1, wherein the glutaredoxin is GRX2.

8. The composition of claim 1, wherein the glutaredoxin is GRX5.

9. The composition of claim 1, further comprising a pharmaceutically acceptable carrier.

10. The composition of claim 1, further comprising an additional therapeutic compound.

11. The composition of claim 10, wherein the additional therapeutic compound is a thioredoxin.

12. A composition, comprising:
a glutaredoxin wherein the glutaredoxin has an identity of greater than 90% with GRX in combination with a pharmaceutically acceptable carrier for pulmonary delivery, wherein glutaredoxin is GRX1, GRX2, GRX5, comprising an inactivated caspase cleavage site comprising Glu-Phe-Val-Asp (SEQ ID NO:9).

13. The composition of claim 12, wherein the glutaredoxin active site comprises Cys-Pro-Tyr-Cys (SEQ ID NO:1), Cys-Ser-Tyr-Cys (SEQ ID NO:2 or Cys-Gly-Phe-Ser (SEQ ID NO:3).

14. The composition of claim 12, wherein the glutaredoxin is a human glutaredoxin.

15. The composition of claim 12, wherein the pharmaceutically acceptable carrier for pulmonary delivery is an aerosol formulation.

16. The composition of claim 12, further comprising an inhaler, wherein the composition is contained in the inhaler.

* * * * *